US007520874B2

(12) United States Patent
Koyama et al.

(10) Patent No.: US 7,520,874 B2
(45) Date of Patent: Apr. 21, 2009

(54) DISPOSABLE DIAPER WITH IMPROVED LEAK PREVENTION PROPERTIES

(75) Inventors: Takao Koyama, Tochigi (JP); Hidekazu Ito, Tochigi (JP); Ken Nemoto, Tochigi (JP); Kenji Ishiguro, Tochigi (JP)

(73) Assignee: Kao Corporation, Tokyo (JP)

( * ) Notice: Subject to any disclaimer, the term of this patent is extended or adjusted under 35 U.S.C. 154(b) by 88 days.

(21) Appl. No.: 11/561,803

(22) Filed: Nov. 20, 2006

(65) Prior Publication Data

US 2007/0093772 A1    Apr. 26, 2007

Related U.S. Application Data

(62) Division of application No. 11/067,249, filed on Feb. 28, 2005, now Pat. No. 7,156,830, which is a division of application No. 10/005,352, filed on Dec. 7, 2001, now Pat. No. 6,878,139.

(30) Foreign Application Priority Data

| Dec. 28, 2000 | (JP) | ............... 2000-402839 |
| Jan. 19, 2001 | (JP) | ............... 2001-11156 |
| Mar. 9, 2001 | (JP) | ............... 2001-66189 |
| Jun. 13, 2001 | (JP) | ............... 2001-178184 |

(51) Int. Cl.
*A61F 13/15* (2006.01)
(52) U.S. Cl. ............... 604/385.27; 604/385.01; 604/385.101
(58) Field of Classification Search ............... 604/378, 604/379, 385.01, 385.23, 385.24, 385.27, 604/385.101, 385.201
See application file for complete search history.

(56) References Cited

U.S. PATENT DOCUMENTS

| 3,575,174 | A |  | 4/1971 | Mogor |
| 4,430,088 | A |  | 2/1984 | Karami |
| 4,657,539 | A |  | 4/1987 | Hasse |
| 4,743,246 | A |  | 5/1988 | Lawson |
| 5,366,453 | A |  | 11/1994 | Zehner et al. |
| 5,382,246 | A |  | 1/1995 | Kawano |
| 5,464,402 | A |  | 11/1995 | Zajaczkowski |
| 5,776,122 | A |  | 7/1998 | Faulks et al. |
| 5,779,690 | A | * | 7/1998 | Gustafsson et al. .... 604/385.19 |

(Continued)

FOREIGN PATENT DOCUMENTS

EP       0880955 A2    12/1998

(Continued)

*Primary Examiner*—Tatyana Zalukaeva
*Assistant Examiner*—Michael G Bogart
(74) *Attorney, Agent, or Firm*—Birch, Stewart, Kolasch & Birch, LLP

(57) ABSTRACT

A disposable diaper comprising a fluid-permeable topsheet, a fluid-impermeable backsheet and a fluid-retentive absorbent core interposed between the topsheet and the backsheet, the disposable diaper being formed in a substantially vertically elongated configuration and having a stomach side, a back side and a crotch region positioned between the stomach side and the back side, wherein a second absorbent core is disposed at an outside region of each opposite side edge of the absorbent core at the crotch region along a longitudinal direction of the diaper, and an elastic member is disposed at the region where the second absorbent core is disposed along a longitudinal direction of the diaper.

9 Claims, 10 Drawing Sheets

U.S. PATENT DOCUMENTS

| | | |
|---|---|---|
| 6,102,892 A | 8/2000 | Putzer et al. |
| 6,126,648 A | 10/2000 | Keck et al. |
| 6,159,190 A | 12/2000 | Tanaka et al. |
| 6,315,766 B1 | 11/2001 | Drevik et al. |
| 6,326,525 B1 | 12/2001 | Hamajima et al. |
| 6,328,724 B1 | 12/2001 | Ronnberg et al. |
| 6,410,822 B1 | 6/2002 | Mizutani et al. |
| 6,436,079 B1 | 8/2002 | Blenke et al. |
| 6,492,574 B1 | 12/2002 | Chen et al. |
| 6,635,040 B1 | 10/2003 | Kim et al. |
| 6,867,345 B2 | 3/2005 | Shimoe et al. |
| 2002/0065499 A1 | 5/2002 | Ohashi et al. |

FOREIGN PATENT DOCUMENTS

| | | |
|---|---|---|
| JP | 52-120045 A | 10/1977 |
| JP | 58-115105 A | 7/1983 |
| JP | 01-119250 | 5/1989 |
| JP | 01-272802 | 10/1989 |
| JP | 2-10824 | 1/1990 |
| JP | 02-291858 | 12/1990 |
| JP | 03-121069 | 5/1991 |
| JP | 03-123553 | 5/1991 |
| JP | 4-67427 A | 6/1992 |
| JP | 4-242643 A | 8/1992 |
| JP | 5-317362 A | 12/1993 |
| JP | 6-17724 U | 3/1994 |
| JP | 9-173381 A | 7/1997 |
| JP | 10-99372 A | 4/1998 |
| JP | 11-99174 A | 4/1999 |
| JP | 11-155901 A * | 6/1999 |
| JP | 2000-15 A | 2/2000 |
| TW | 349387 | 1/1999 |
| TW | 376315 | 12/1999 |
| WO | WO 95/25493 A1 * | 9/1995 |

* cited by examiner

DISPOSABLE DIAPER WITH IMPROVED LEAK PREVENTION PROPERTIES This application is a Divisional of application Ser. No. 11/067,249 filed on Feb. 28, 2005, now U.S. Pat. No. 7,156,830 which is a Divisional of prior application Ser. No. 10/005,352 filed on Dec. 7, 2001, which has now issued as U.S. Pat. No. 6,878,139, and for which priority is claimed under 35 U.S.C. § 120; and this application claims priority of application Ser. Nos. 2000-402839, 2001-11156, 2001-66189 and 2001-178184 filed in Japan on Dec. 28, 2000, Jan. 19, 2001, Mar. 9, 2001 and Jun. 13, 2001, respectively, under 35 U.S.C. § 119; the entire contents of all are hereby incorporated by reference.

BACKGROUND OF THE INVENTION

This invention relates to a disposable diaper excellent in leak-preventive property and capable of preventing leak occurrable particularly around the leg areas. This invention also relates to a disposable diaper excellent in storability/retainability of an auxiliary absorber, wearability (property of feel in wear and easy application to a wearer) and/or fitness at the crotch region and the like, in addition to its excellent leak-preventive property.

Heretofore, it has been an important problem for disposable diapers how to prevent leak occurrable around the leg areas. Japanese Patent Publication No. 05-33630 discloses a disposable diaper in which an absorbent core is comprised of a central absorbent section of a width in conformity with the human body and an outer absorbent section disposed outside thereof, so that close fit to a wearer at the crotch region is enhanced, thereby improving the leak-preventive property. However, this disposable diaper has such a problem that wrinkles are liable to occur to the central absorbent section due to contraction of an expansible part placed between the central absorbent section and the outside absorbent section, and therefore urine and excretions can easily leak from the central absorbent section along the wrinkles. Moreover, since it is designed such that leak is prevented by enhancing the fit at the central absorbent section, those urine and excretions leaked out towards the opposite sides from the central absorbent section can reach the outside absorbent section comparatively easily, and especially, in case the amount of excretions is large, those feces and urine easily leak outside beyond the outside absorbent section.

Moreover, since the outside absorbent section is difficult to deform along the contour of the wearer's body, wearability and fitting property at the crotch region are deteriorated.

Japanese Patent No. 2712044 discloses a disposable diaper in which three-dimensional guards each composed of an absorbent material are disposed at the outside of the an absorbent core in a longitudinal direction thereof. This diaper also has the same problem as the above-mentioned disposable diaper.

Another problem of the disposable diaper of Japanese Patent Publication No. 05-33630 is that it is not easy for a wearer to put it on because this diaper does not deform to the curved configuration of the wearer's body at the time of putting it on.

In the disposable diaper of Japanese Patent Publication No. 05-33630, the outside absorbent section is brought into contact with the inner side of the wearer's upper thigh. However, in this disposable diaper, the outside absorbent section is liable to be turned over at an area in the vicinity of the boundary area between a stomach side region and/or the back side region where the central absorbent section and the outside absorbent section are placed on a same plane and brought into contact with the wearer and the crotch region where the outside absorbent section and the central absorbent section are greatly bent, and leak may occur through a gap formed between the outside absorbent section and the wearer's skin. Moreover, it is difficult for this disposable diaper to sufficiently fit with the outside absorbent section to the inner side of the wearer's upper thigh. In short, in the conventional disposable diapers, sufficient leak-preventive property is not yet realized even for those of the type of which an absorbent core is disposed around the leg area.

Recently, it was attempted in order to reduce the economical/laborious burden in nursing work or the like that an auxiliary absorber is used in combination with a disposable diaper. However, the conventional disposable diaper is deteriorated in storability/retainability of the auxiliary absorber and its improvement is demanded.

Japanese Patent Application Laid-Open No. 01-119250, Japanese Utility Model Application Laid-Open No. 04-67427 and Japanese Utility Model Application Laid-Open No. 02-18824 disclose disposable diapers having a side absorbent core. However, even in those disposable diapers, the side absorbent core cannot fit to the wearer's leg area sufficiently. Furthermore, even in disposable diapers disclosed in Japanese Patent Application Nos. 03-121069 and 03-123553, sufficient leak-preventive property cannot be achieved.

SUMMARY OF THE INVENTION

It is, therefore, a first object of the present invention to provide a disposable diaper excellent in leak-preventive property and capable of surely preventing leak occurrable around the leg areas.

A second object of the present invention is to provide a disposable diaper excellent in leak-preventive property and excellent in storability/retainability of an auxiliary absorber.

A third object of the present invention is to provide a disposable diaper capable of taking such a curved configuration as being able to fit to the wearer's body at the time of putting it on and therefore, capable of being worn very easily.

A fourth object of the present invention is to provide a disposable diaper capable of fitting its second absorbent core disposed portion having a fluid retainability closely to the wearer's skin, excellent in fitness to the inguinal area and capable of surely preventing leak occurrable around the leg areas.

A further object of the present invention is to provide a disposable diaper excellent in storability/retainability of an auxiliary absorber, and excellent in wearability (property of easy application to a wearer) and fitness at the crotch region, in addition to its excellent leak-preventive property.

A still further object of the present invention is to provide a disposable diaper capable of taking the shape of a trunks, excellent in leak-preventive property and designability, and easy to put on or apply to a wearer.

The present invention has achieved the above-mentioned first object by providing a disposable diaper comprising a fluid-permeable topsheet, a fluid-impermeable backsheet and a fluid-retentive absorbent core interposed between the topsheet and the backsheet, the disposable diaper being formed in a substantially vertically elongated configuration and having a stomach side, a back side and a crotch region positioned between the stomach side and the back side, wherein a second absorbent core is disposed at an outside region of each opposite side edge of the absorbent core at the crotch region along a longitudinal direction of the diaper, and an elastic member is disposed at the region where the second absorbent core is disposed along a longitudinal direction of the diaper (the "first invention" used hereinafter refers to this invention).

Also, the present invention has achieved the above-mentioned second and/or third object by providing a disposable diaper comprising a fluid-permeable topsheet, a fluid-impermeable backsheet and a fluid-retentive central absorbent core interposed between the topsheet and the backsheet, the disposable diaper being formed in a substantially vertically elongated configuration and having a stomach side, a back side and a crotch region positioned between the stomach side and the back side, wherein a second absorbent core is disposed at an outside region of each opposite left (or right) side edge of the central absorbent core at the crotch region along a longitudinal direction of the diaper, a basis weight of an absorbent core disposed at an intermediate region between the central absorbent core and each of the second absorbent cores is smaller than a basis weight of any of the absorbent cores located at the region where the central absorbent core is disposed and at the region where each of the second absorbent cores is disposed, and a pair of axes of flexibility are formed on opposite side portions of the central absorbent core along a longitudinal direction (the "second invention" used hereinafter refers to this invention).

The present invention has achieved the above-mentioned fourth object by providing a disposable diaper comprising a fluid-permeable topsheet, a fluid-impermeable backsheet and a fluid-retentive absorbent core interposed between the topsheet and the backsheet, the disposable diaper having a stomach side, a back side and a crotch region positioned between the stomach side and the back side, leg portion elastic members being disposed in their stretched states at a pair of leg portions disposed around the wearer's leg areas, wherein lengthwise opposite end portions of the leg portion elastic members are located at widthwise outside areas of side edges of the absorbent core, respectively and central portions of the leg portion elastic members are curved in such a manner as to pass a widthwise inner direction of the side edges of the absorbent core at a crotch region of the diaper, the absorbent core at the crotch region of the diaper is divided into a pair of second absorbent cores located at widthwise outside areas of the leg portion elastic members, respectively and a central absorbent core located between the pair of second absorbent cores by the pair of leg portion elastic members, and the second absorbent cores are, when in wear, bent towards the backsheet (the "third invention" used hereinafter refers to this invention).

BRIEF DESCRIPTION OF THE DRAWINGS

The present invention will be more particularly described with reference to the accompanying drawings, in which.

DETAILED DESCRIPTION OF THE PREFERRED EMBODIMENTS

Figure 1:
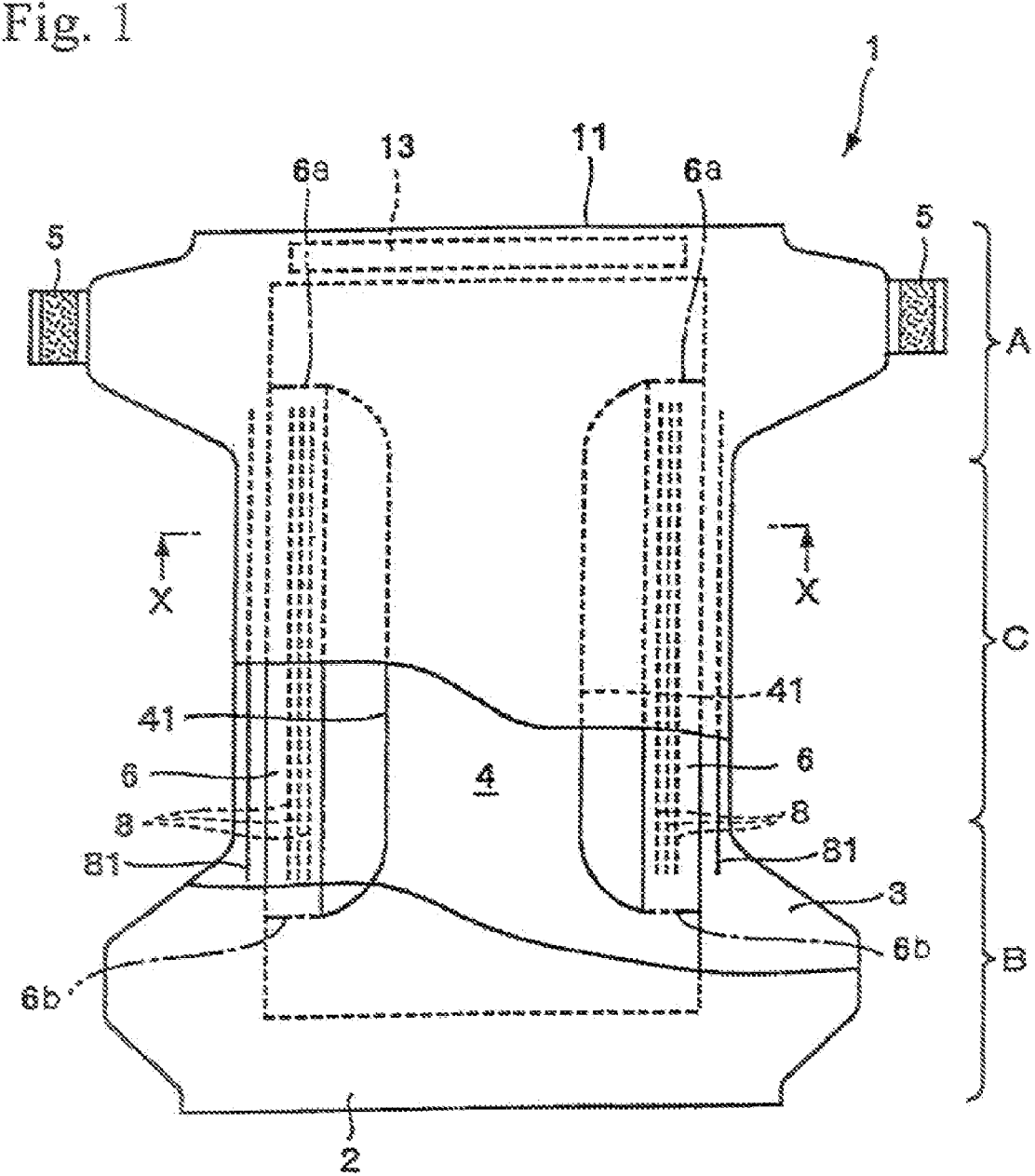
FIG. 1 is a plan view showing, partly cut-away, a disposable diaper according to one embodiment of the first invention.
Figure 2:
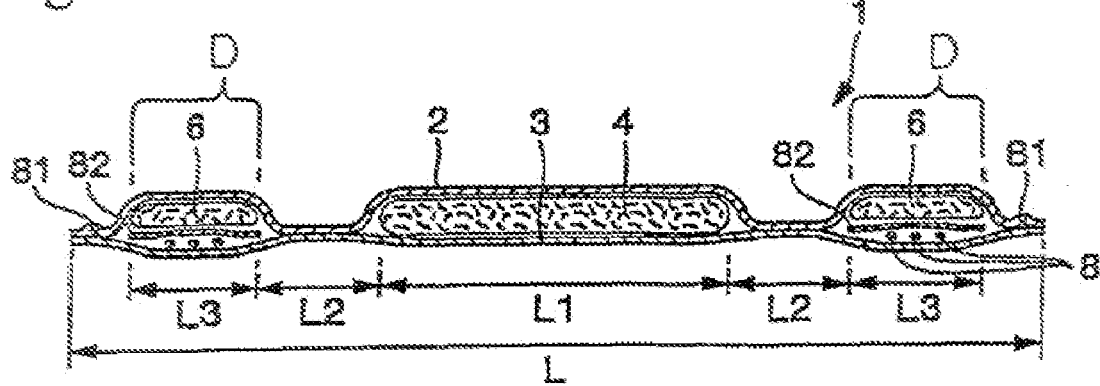
FIG. 2 is a schematic sectional view taken on line X-X of FIG. 1.
Figure 3:
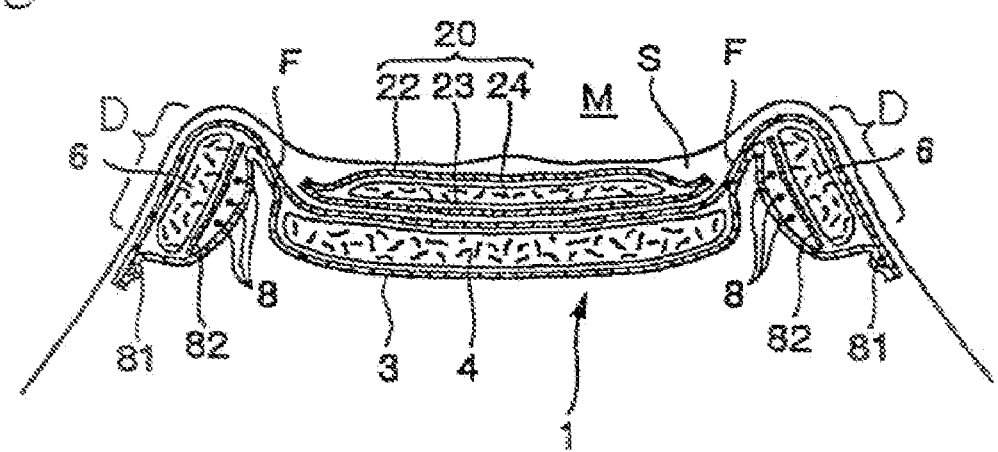
FIG. 3 is a schematic sectional view showing a using state of the disposable diaper of FIG. 1.

Preferred embodiments of the present invention will be described hereinafter. A disposable diaper 1 according to a first embodiment of the first invention comprises, as shown in FIGS. 1 to 3, a fluid-permeable topsheet 2, a fluid-impermeable backsheet 3 and a central absorbent core 4 as a fluid-retentive absorbent core interposed between the topsheet 2 and the backsheet 3, the disposable diaper 1 being formed in a substantially vertically elongated configuration.

The topsheet 2 and the backsheet 3 each have an external configuration equal to that of the disposable diaper 1, in which a lengthwise central portion is constricted. The central absorbent core 4 as an absorbent core is interposed between the topsheet 2 and the backsheet 3, and it has a hourglass-like configuration whose lengthwise central portion is constricted. A waist portion elastic member 13 for forming a waist gather is disposed at a back side region A which is located at the back side of the wearer in wear along a back side waist edge portion (that portion forming an opening edge portion on a back side of a waist opening portion which is formed when in wear) 11. Fastening tapes 5, 5 are disposed at opposite side edges of the back side region A, respectively. Landing zones (not shown) for fixing the fastening tapes 5, 5 are disposed at an outer surface of a stomach side region B which is disposed at the wearer's stomach side when in wear.

A crotch region C in the disposable diaper 1 is a portion which is disposed at the wearer's crotch in wear and is located between the back side region A and the stomach side region B. Fluid retentive second absorbent cores 6, 6 are disposed at outside areas of opposite side edges 41, 41 of the central absorbent core 4 in the crotch region C in such a manner as to be spaced apart from the opposite side edges 41, 41, respectively. The second absorbent cores 6, 6 each have a belt-like configuration and are disposed along a longitudinal direction of the diaper 1. More specifically, the second absorbent core 6 is approximately equal in width over its longitudinal direction in the crotch region C and is disposed such that its longitudinal direction is aligned with a longitudinal direction of the diaper 1. The second absorbent cores 6, 6 are disposed between the back side region A and the stomach side region B and are integrally connected to the central absorbent core 4 at opposite end portions 6*a*, 6*b* thereof, respectively.

As the second absorbent core 6, those conventional ones having various constitutions and used as an absorbent core in an absorbent article such as disposable diaper or the like can be used without any particular limitation. For example, there can be used an aggregate of hydrophilic fibers composed of a natural material such as, rayon, cellulose or the like, an aggregate obtained by surface treating synthetic fibers such as polyethylene, polypropylene or the like, any of those aggregates with a water absorption polymer retained thereby, and the like.

In the disposable diaper of the first invention, an elastic member 8 is disposed at each region D (see FIGS. 2 and 3) where the second absorbent core 6 is disposed, along a longitudinal direction of the diaper 1. The "region D" where the second absorbent core 6 is disposed refers to a region, at the inside of which the second absorbent core 6 is arranged when the disposable diaper is developed and plan viewed as shown in FIG. 1. In the disposable diaper 1 of this embodiment, as shown in FIG. 2, plural pieces of elastic members 8 are disposed between the second absorbent core 6 and the backsheet 3 in the region D where the second absorbent core 6 is disposed. Each elastic member 8 is fixedly sandwichingly held between the backsheet 3 and a fixing sheet 82 disposed on the backsheet 3 in an stretched state thereof.

The second elastic member 81 is disposed at an outside area of the region D where the second absorbent core 6 is disposed in a widthwise direction of the disposable diaper 1, i.e., in an outside area of the region D where the second absorbent core 6 is disposed, in a widthwise direction of the diaper 1 when plan viewed in a developed state of the diaper 1 as shown in FIG. 1, along a longitudinal direction of the diaper 1. One piece each of the second elastic member 81 is disposed at an edge portion of each opposite left (or right) side and is fixedly sandwichingly held, as shown in FIG. 2, between the topsheet 2 and the backsheet 3 in its stretched state.

The elastic members 8 disposed at the region D and the second elastic member 81 disposed at the outside region are each arranged over the length between the back side region A and the stomach side B and in parallel with each other.

The material for forming the various members of the disposable diaper 1 of this embodiment will now be described. As the material for forming the topsheet 2, the backsheet 3, the central absorbent core 4, the fastening tape 5, the waist elastic member 13 and the landing zone (not shown), various kinds of those which have heretofore been used for disposable diapers can be used without any particular limitation. As the raw material for forming the elastic members 8 and the second elastic member 81, those of various kinds such as natural rubber, synthetic rubber, spandex and the like can be used. Their shapes may be in the form of thread, belt, film or the like.

The disposable diaper 1 of this embodiment is applied to the wearer for use in the same manner as the normal disposable diapers. According to the disposable diaper 1 of this embodiment, since the elastic members 8 are disposed at the regions D where the second absorbent cores 6 are disposed, the skin side surfaces of the regions D where the second absorbent cores 6 are disposed nicely fit around the leg areas of the wearer M, as shown in FIG. 3. For this reason, even if urine, etc. should leak out to the side of the central absorbent core 4, they would surely be absorbed by the second absorbent cores 6 without allowing them to reach the side edge portion of the diaper 1. Consequently, leak of the excretions, particularly leak of urine around the leg areas, can surely be prevented.

Moreover, since the central absorbent core 4 and the second absorbent cores 6, 6 are divided from one another at the crotch region C, wrinkles hardly occur to the central absorbent core 4 even if the elastic members 8 are contracted. This makes it possible to prevent urine, etc. from migrating in a lateral direction along the wrinkles which would otherwise be formed on the central absorbent core 4. In addition, the above makes it possible to fully exhibit the absorption capability of the central absorptive core 4. Accordingly, leak of urine, etc. can be prevented more effectively.

In the disposable diaper 1 of this embodiment, since the second elastic members 81 are disposed at the outside areas of the regions D where the second absorbent cores 6, 6 are disposed, the urine absorbed by the second absorbent cores 6, 6 can be prevented from leaking from the side edges.

In the disposable diaper 1 of this embodiment, since the central absorbent core 4 and the second absorbent cores 6, 6 are individually spaced apart from one another, those regions F, F, which are, when in wear, located between the central absorbent core 4 and the second absorbent cores 6 of the diaper 1 are, as shown in FIG. 3, angularly stood up with respect to the wearer's skin surface and are functioned as three-dimensional barriers for the prevention of leak from those areas. Accordingly, the leak-preventive property, particularly leak-preventive property around the leg areas is further enhanced. Moreover, since the regions F, F located between the absorbent core 4 and the second absorbent cores are stood up, a receiving space S having a shape capable of retaining an auxiliary absorber 20 can easily be formed on an inner surface of the disposable diaper 1. Accordingly, the displacement occurrable to the auxiliary absorber 20 when the auxiliary absorber 20 is disposed on the inner surface of the disposable diaper 1, can be prevented effectively. Moreover, the arrangement or replacement of the auxiliary absorber 20 can be carried out very easily and rapidly.

The absorbent core may be disposed at the region F located between the central absorbent core 4 and each second absorbent core 6. From the view point of enhancing the standing propensity of the region F, however, the weight per unit area of the region F is preferably $2/3$ or smaller than the weight per unit area of the region D where the second absorbent core 6 is disposed. The weight per unit area of the region F located between the central absorbent core 4 and each second absorbent core 6 and the weight per unit of the region D where the second absorbent core 6 is disposed can be obtained as follows, respectively. Test pieces of 1 cm×1 cm cut out from the region F and the region D in the disposable diaper, respectively. Then, the weights of the test pieces are measured.

Figure 7:
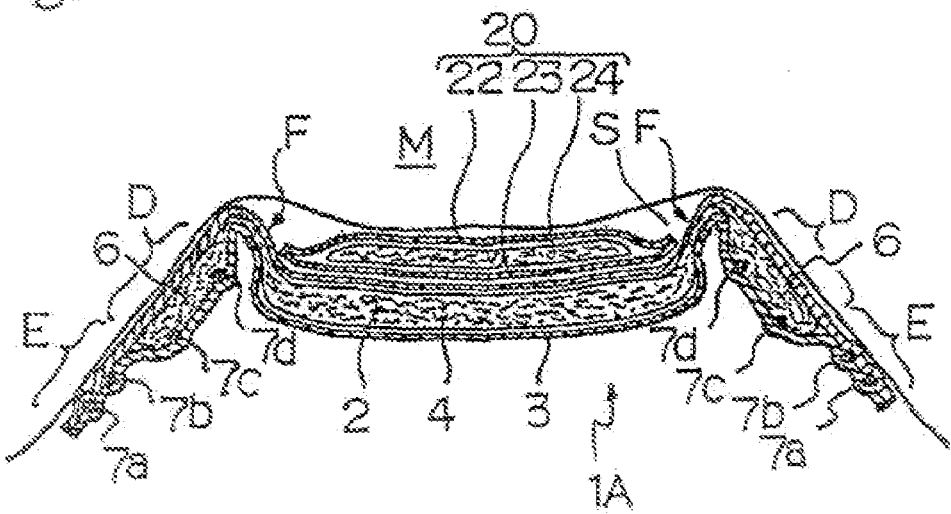
FIG. 7 is a schematic sectional view showing a using state of the disposable diaper of FIG. 4.

The auxiliary absorber 20 of FIGS. 3 and 7 is a substantially vertically elongated absorptive pad (auxiliary pad) comprising a fluid-permeable topsheet 22, a fluid-impermeable backsheet 23 and a fluid-retentive absorbent core 24 interposed between the topsheet 22 and the backsheet 23. This auxiliary absorber 20 is disposed on an inner surface of the diaper such that its longitudinal direction is aligned with a longitudinal direction of the disposable diaper.

From the view point of exhibiting at least one of the above-mentioned effects efficiently, the width L (see FIG. 2) of the central absorbent core 4 is preferably from 5 to 25 cm, the distance L2 between the central absorbent core 4 and each second absorbent core 6 is preferably from 0.5 to 10 cm and the width L3 of the second abosrbent core 6 is preferably from 1 to 10 cm, all at the crotch region C of the disposable diaper 1. Also, from the same view point, the ratio (L1/L) of the width L1 of the central absorbent core 4 with respect to the smallest width L of the disposable diaper 1 at the crotch region C is preferably from 0.1 to 0.8, the ration (L2/L) of the distance L2 between the central absorbent core 4 and each second absorbent core 6 with respect to the smallest width L of the disposable diaper 1 is preferably from 0.01 to 0.3 and the ratio (L3/L) of the width L3 of the second absorbent core 6 with respect to the smallest width L of the disposable diaper 1 at the crotch region C is preferably from 0.02 to 0.3. The dimensions of the various portions and the ratios are dimensions obtained by measurement carried out in a state in which the diaper is developed and planarly spread as shown in FIG. 1 and the ratios based thereon.

The present invention is not limited to the above-mentioned embodiment and it can be changed or modified in accordance with necessity and without departing from the gist of the invention. For example, it is accepted that the central absorbent core 4 and the second absorbent cores 6 are not spaced apart form each other and that they are adjacent to each other through a slit. Moreover, the second absorbent cores 6, 6 may be formed as completely separate bodies from the central absorbent core 4. In other words, the second absorbent cores 6, 6 and the central absorbent core 4 may be divided over the lengthwise entire area of the central absorbent core 4.

It is also accepted that an absorptive material having a smaller weight per unit area than the central absorbent core 4 and the second absorbent cores 6 is disposed at the region F between the central absorbent core 4 and each second absorbent core 6. For example, it is accepted that an absorbent core having a small width is laminated on an absorbent core having a large width at a widthwise center thereof and opposite side edge portions of the large width absorbent core are folded back towards the surface of the large width absorbent core on which the small width absorbent core is laminated, so that a predetermined gap is formed between the opposite side edge portions of the small width absorbent core and the opposite side edge portions of the large width absorbent core.

The elastic member 8 at the region D where the second absorbent core 6 is disposed may be disposed at any part in a thickness direction of the region D. For example, the elastic member 8 may be disposed between the topsheet 2 and the second absorbent core 6, or within the second absorbent core 6, or at the outer surface of the backsheet 3. The elastic member 8 is preferable disposed at a location on the more outer surface side of the diaper than the second absorbent core 6. The number of the elastic members 8 and the second absorbent cores 81 is not particularly limited. The number may be only one or plural. The configuration, dimension, forming material, etc. of each part of the disposable diaper can be changed in accordance with necessity. The disposable diaper of the present invention is especially suited to be used as a diaper for an adult person. The same effect can be obtained when the present invention is applied to a case where no auxiliary absorber is employed.

The disposable diaper of the first invention is excellent in leak-preventive property and is capable of surely preventing the leak (side leak) particularly around the leg areas.

A second embodiment of the first invention will be described with reference to FIGS. 4 to 7. The same explanation as in the first embodiment will be omitted.

In the disposable diaper 1A according to this embodiment, the second absorbent cores 6, 6 are integral with the central absorbent core 4 through the absorbent core (the absorbent core disposed at the intermediate region F) having a lower basis weight than the second absorbent cores 6, 6. In more detail, the central absorbent core 4 and the leg absorbent cores 6, 6 are segmented by intermediate regions F, F provided with the absorbent cores whose basis weights are lower than the basis weights of the central and leg absorbent cores 6, 6 and 4 (see FIG. 5). The regions D where the second absorbent cores 6 are disposed are referred to as the leg absorbent portions D hereinafter.

The topsheet 2 and the backsheet 3 in the disposable diaper 1A according to this embodiment are further extended outwardly in the widthwise direction from the position where the outer edge 61 of the second absorbent core 6 is located, and edge flap portions E, E are formed at opposite side edge portions of the diaper 1A by the extended parts of the topsheet 2 and the backsheet 3. In the disposable diaper 1A according to this embodiment, a plurality of elastic members 7a to 7d are disposed at the edge flap portions E and the leg absorbent portions D on opposite left and right sides of the diaper 1A along a longitudinal direction of the diaper. Specifically, two elastic members 7a, 7b are disposed at each edge flap portion E, and two elastic members 7c, 7d are disposed at each leg absorbent portion D. The elastic members 7a, 7b are fixedly sandwichingly held between the topsheet 2 and the backsheet 3 which constitute the edge flap portion E, and the elastic members 7c, 7d are fixedly sandwichingly held between the second absorbent core 6 and the backsheet 3.

In the disposable diaper according to the second embodiment, the lengthwise shrinkage of the edge flap portion E in the crotch region C on the opposite left and right sides in the longitudinal direction is larger than the lengthwise shrinkage of the leg absorbent portion D. The shrinkage of the edge flap portion and the shrinkage of the leg absorbent portion D in the longitudinal direction are measured as follows, respectively.

<Method for Measuring Shrinkage>

Figure 4:
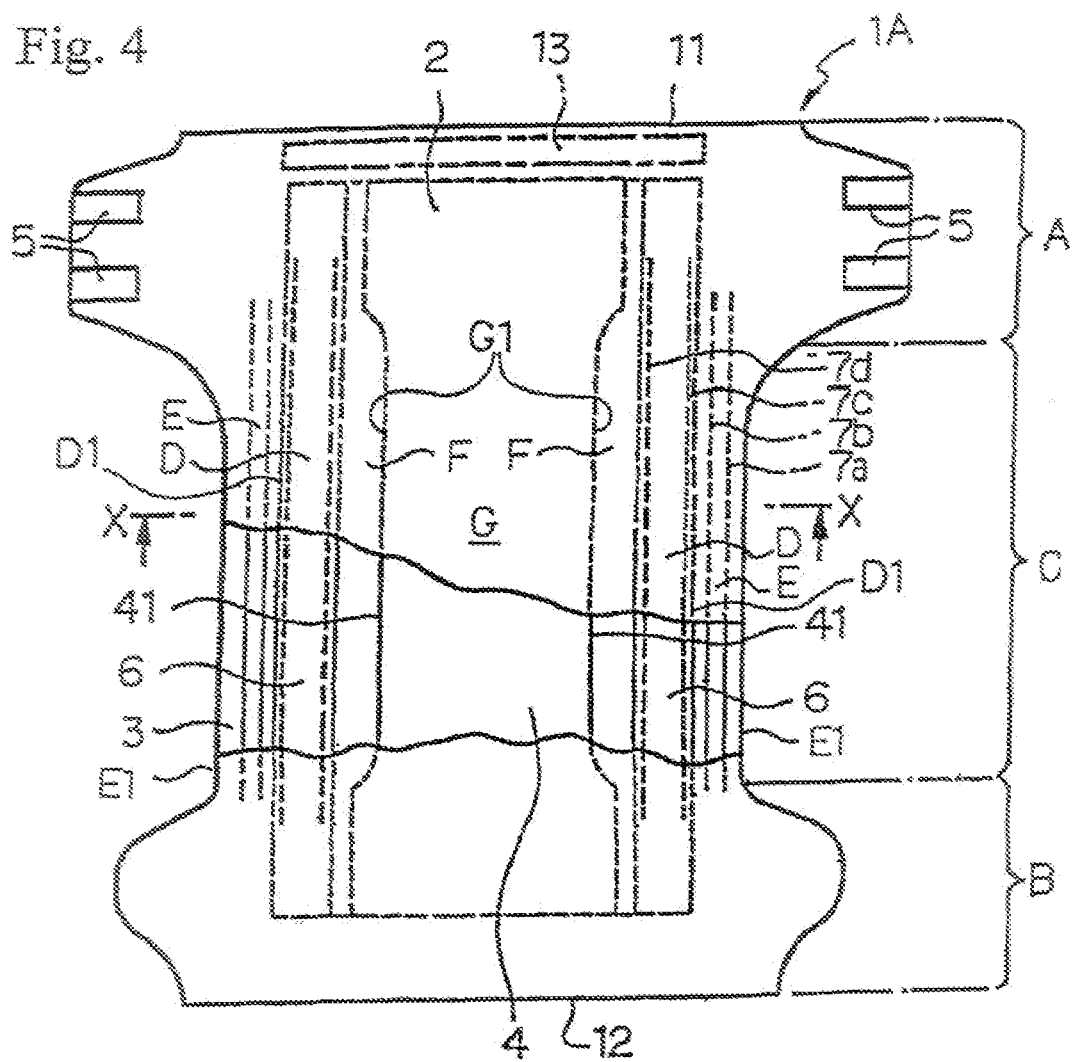
FIG. 4 is a plan view showing, partly cut-away, a disposable diaper according to another embodiment of the first invention.
Figure 5:
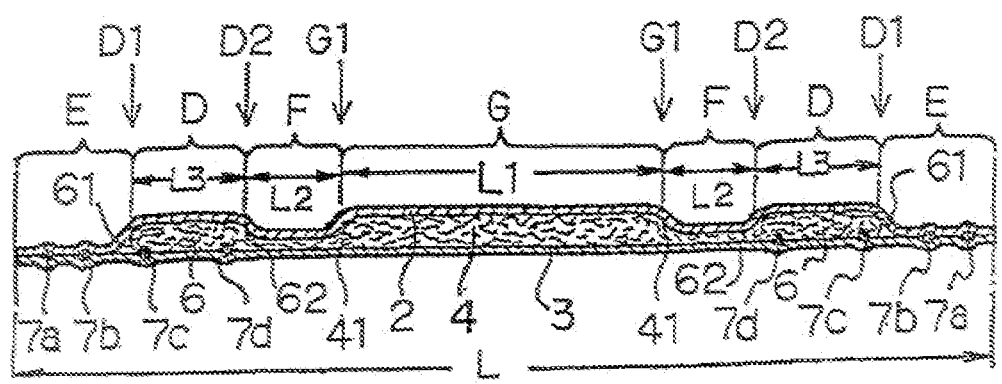
FIG. 5 is a schematic sectional view taken on line X-X of FIG. 4.

The disposable diaper is held in a tensioned state (the state in which the elastic members at various portions are stretched and planarly spread) as shown in FIG. 4. In that state, two points are defined on an outer edge E1 of the edge flap portion E and on an inner side edge D2 (the same as on the inner side edge 62 of the second absorbent core 6) of the leg absorbent portion D in the crotch region C, respectively. Then, a shortest distance in a longitudinal direction between the two points is represented by a.

Then, the tensioned state is released, and a shortest distance between the two points in a state (natural state) in which no external force is exerted thereto is represented by b.

The shrinkage can be obtained by using the following equation.

$$\text{shrinkage } (\%) = \{(a-b)/a\} \times 100$$

The shrinkage at the outer edge of the edge flap portion is regarded as the "shrinkage at the edge flap portion E" and the shrinkage at the inner side edge of the leg absorbent portion D is regarded as the "shrinkage at the leg absorbent portion".

The two points taken on the side edge of the edge flap portion E and on the inner side edge of the leg absorbent portion D are, in principle, decided by taking one point on a border line between the crotch region C and the back side region A and another one point on a border line between the crotch region C and the stomach side region B. The crotch region C in the disposable diaper according to this second embodiment refers to the "two inside regions" of all four regions which are obtained by dividing the disposable diaper into four equal parts in a longitudinal direction of the diaper.

From the view point of enhancing the leak-preventive property, feel during wear, storability/retainability of the auxiliary absorber, fitness at the crotch region attributable to the enhancement and effect of formability of the leak-preventive barrier formed by bending the leg absorbent portion D, the ration (P/Q) of the shrinkage P of the edge flap portion E with respect to the shrinkage Q at the leg absorbent portion D is preferably from 1.1 to 3.0, and particularly preferably from 1.3 to 2.0. Also, from the same view point, the shrinkage at the edge flap portion E is preferably from 20 to 70%, and particularly preferably from 30 to 60%, and the shrinkage at the edge flap portion E is preferably from 5 to 55%, and particularly preferably from 15 to 45%.

In the disposable diaper 1A, the leg absorbent portion D takes a curved form, as later described, in its natural state owing to the feature that the shrinkage at the edge flap portion E in the longitudinal direction is larger than the shrinkage at the leg absorbent portion D in the longitudinal direction. Even in a case where no elastic member is disposed at the edge flap portion E, the leg absorbent portion D can be protuberatingly curved inward, for example, by applying a high elasticity to the leg absorbent portion D at the area offset to the outer edge thereof and by extremely reducing the rigidity of the edge flap portion compared with the rigidity of the leg absorbent portion D. However, it is preferred that the elastic member is disposed at the edge flap portion E from the view point of surely obtaining the above-mentioned curve, surely exhibiting the enhancement and effect of the formability of the leak-preventive barrier, storability/retainability of the auxiliary absorber, etc., fitness around the leg areas, and the like, and further enhancing the above-mentioned effect. In the case where the elastic member is disposed at the edge flap portion E, the shrinking force of the elastic member is never lost by the shrinkage of the leg absorbent portion D.

Figure 6:
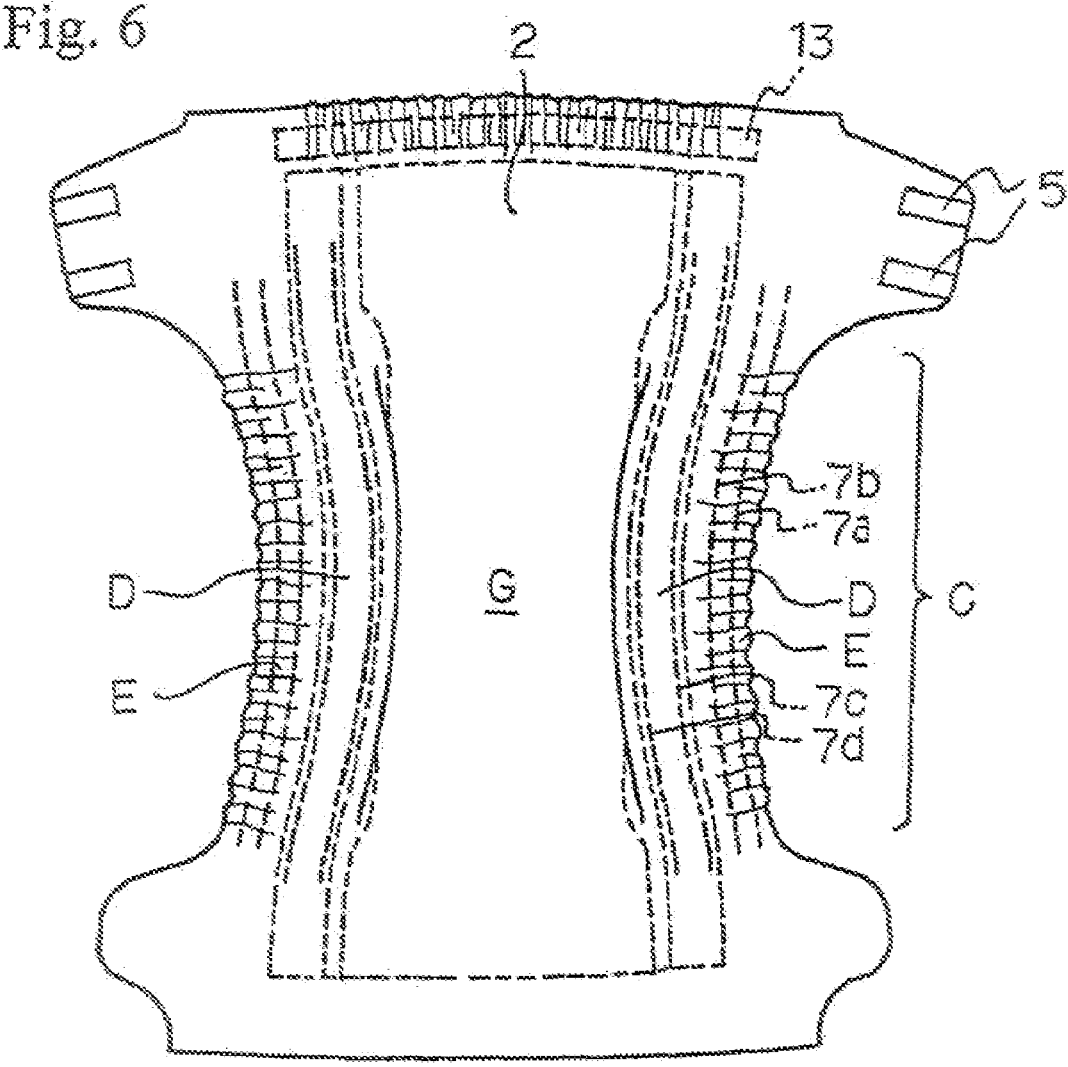
FIG. 6 is a plan view (bird's eye view) showing a natural state of the disposable diaper of FIG. 4 in which its topsheet side (that surface side facing the wearer's skin) faces upward.

In a natural state of the disposable diaper 1A as shown in FIG. 6, the leg absorbent portions D, D are protuberatingly curved inward in a widthwise direction of the diaper. The natural state used herein refers to a state in which the disposable diaper is placed on a horizontal plane and left as it is (the state in which the stretched state of each elastic member is released) with its topsheet side (that surface side facing the wearer's skin) faced upward. In the disposable diaper 1A according to this embodiment, the leg absorbent portions D, D are curved in such a manner as to form an arc as a whole.

In the disposable diaper 1A according to this embodiment, a shrinking force damping region having a predetermined width is formed between the central absorbent portion (referred to as the region provided with the central absorbent core 4) G and each of the leg absorbent portions D, D at least in the crotch region. In this embodiment, the intermediate regions F, F are the shrinking force damping regions. The shrinking force damping region used herein refers to a region where its lengthwise inner side edge is small in shrinkage and its lengthwise outer edge is large when compared with a case in which the region is composed of the leg absorbent portion D. By providing such a shrinking force damping region, twisting which would otherwise occur to the central absorbent portion G can be prevented by buffering the shrinking force conveyed from the leg flap portion (the region formed by a combination of the leg absorbent portion D with the edge flap portion E). Moreover, by sandwiching the leg absorbent portion D between the edge flap portion E having a large shrinkage and the shrinking force damping region having a small shrinkage, the curve of the leg absorbent portion D in the crotch region C can surely be achieved. That is, the leg absorbent portions D, D can surely be curved in such a manner as to be constricted inward at the nearby area of the shrinking force damping region in the crotch region C, thereby further enhancing the formability of the leak-preventive barrier and the storability/retainability of the auxiliary absorber, etc. As a method (means) for forming the shrinking force damping region, the area between the central absorbent portion G and each leg absorbent portion D may be composed of (a) a material (plural members are also accepted) having a lower rigidity than the leg absorbent portion D (for example, a absorbent core having a lower basis weight than the second absorbent core 6 is disposed between the topsheet and the backsheet, or not absorbent core is disposed therebetween), or (b) a cushion material such as urethane capable of absorbing the shrinking force (a cushion material may also be disposed between the topsheet and the backsheet). In this embodiment, an absorbent core having a lower basis weight than the central absorbent core 4 and the second absorbent core 6 is disposed between the topsheet 2 and the backsheet 3. The shrinkage at the shrinking force damping region in its longitudinal direction is obtained by the measuring the shrinkage at the inner side edge of the shrinking force damping region (same as the outer edge G1 of the central absorbent portion G) in the same manner as the above-mentioned method for measuring the shrinking force at the leg absorbent portion D, etc.

In the case where the shrinking force damping region is provided, an elastic member may be disposed at the shrinking force damping region inasmuch as the shrinkage of the elastic member is smaller than the shrinkage of the leg absorbent portion D. However, from the view point of preventing the twisting occurrable to the central absorbent portion G, it is preferred that no elastic member is disposed at the shrinking force damping region.

The material of the elastic members 7a to 7d are preferably thread rubber, or flat rubber and particularly preferably flat rubber from the view point of shrinkability around the leg areas, machinability and cost.

The disposable diaper 1A according to the second embodiment is applied to the wearer in the same manner as the normal flat type disposable diapers. According to the disposable diaper 1A of this second embodiment, since the leg absorbent portions D, D are protuberatingly curved inward in a widthwise direction of the diaper, the intermediate portions F, F, which are, when in wear, located between the central absorbent portion G and the leg absorbent portions D, are, as shown in FIG. 7, angularly stood up with respect to the wearer's skin surface and are functioned as leak-preventive barrier (three-dimensional barriers). Accordingly, this disposable diaper 1A is excellent in leak-preventive property, particularly leak-preventive property around the leg areas.

Moreover, since the intermediate portions F, F located between the central absorbent portion G and the leg absorbent portions D are stood up, pockets S having a recessed form and capable of stably retaining the auxiliary absorber 20 are formed in an inner surface of the disposable diaper 1A. Accordingly, the storability/retainability of the auxiliary absorber 20 obtainable when the auxiliary absorber 20 is disposed on the inner surface of the disposable diaper 1 for use in combination, is enhanced. For example, even in case the auxiliary absorber 20 has no fixing means, displacement hardly occurs when in wear. Moreover, the arrangement or replacement of the auxiliary absorber 20 can be carried out very easily and rapidly.

Moreover, since the leg absorbent portions D, D are fit around the leg areas in such a manner as to be protuberatingly curved inward in a widthwise direction of the diaper, the diaper is easy to put on or apply and is excellent in fitness at the crotch region.

In the disposable diaper 1A according to this embodiment, since the elastic members 7c, 7c are also disposed at the leg absorbent portions D along a longitudinal direction of the diaper, the skin side surfaces of the leg absorbent portions D nicely fit around the leg areas of the wearer M, as shown in FIG. 7. For this reason, even if the urine, etc. should leak out to the side of the central absorbent portion, they would surely be absorbed by the leg absorbent portion D without allowing them to reach the side edge portion of the diaper 1. Moreover, since the elastic members 7a, 7b are also disposed at the edge flap portion E located at an outside area of the leg absorbent portion D, duplex leak preventing means is formed at the crotch region. Thus, leak of the excretions from the crotch region can more surely be prevented. Owing to the feature that the elastic members 7c, 7d are disposed at the leg absorbent portion D and the shrinking force damping region (intermediate region F) is formed between the leg absorbent portion D and the central absorbent portion G, the leg absorbent portion D is more surely curved inward at a peripheral area of the shrinking force damping region in the crotch region and the formability of the leak-preventive barrier and retainability of the auxiliary absorber such as auxiliary pad are extensively enhanced.

In the case where the elastic members are disposed at the leg absorbent portion D, the elastic members may be disposed at any part in the thickness direction at the regions. From the view point of surely fitting the specific region to the thigh portion or from the view point of preventing the leg absorbent portion D from falling towards the inner surface side of the diaper, the elastic members are preferably disposed more on the outer surface side than the second absorbent core 6 in the thickness direction. At that time, from the view point of preventing the deterioration of the shrinking force due to detachment of the elastic members, it is preferred that a fixing sheet (not shown) is disposed at the reverse surface side of the second absorbent core in such a manner as to be in abutment with the second absorbent core and the elastic members are fixedly sandwichingly held between the fixing sheet and the reverse surface sheet.

In the disposable diaper 1A according to this embodiment, since at least one pair of fastening tapes as fixing means are disposed at the opposite left and right side edge portions of the back side region A and the waist portion elastic member 13 for forming a waist gather is disposed at an area in the vicinity of the waist opening edge portion 11 in the back side region A, the disposable diaper 1A is very easy to put on or apply. That is, although there is such a fear that when the leg absorbent portion D is curved, the back side flaps forming the opposite side edge portions in the back side region where the fixing mean is disposed are slanted towards the crotch region depending on the degree of the curve, with the result that wearability is lowered, the back side flaps can be prevented from slanting towards the crotch region C by forming a waist gather at an area in the vicinity of the waist opening edge portion 11 so as to provide expanding/contracting property. Moreover, by disposing the waist gather, it becomes possible not only that the effect of leak prevention around the leg areas is enhanced but also that leak from the waist opening portion is more surely prevented. From the view point of enhancing the effect of leak prevention, the waist elastic member is preferably disposed at the stomach side region B, too, as in the back side region A.

From the view point of exhibiting at least one of the above-mentioned various effects effectively, the preferable ranges of the width of the various portions and the ratio of the width of the various portions in the crotch region of the disposable diaper 1A, are preferably the same as those of the disposable diaper 1 according to the first embodiment.

The disposable diaper according to this second embodiment is excellent in storability/retainability of the auxiliary absorber in case the leak preventability and the auxiliary absorber are employed in combination. Also, the diaper according to the second embodiment is excellent wearability and fitness at the crotch region.

A third embodiment of the first invention will be described hereinafter with reference to FIGS. 8 to 11. A disposable diaper 1B according to this third embodiment is designed such that it takes, especially, the shape of trunks when in wear. About those points which are not particularly described or shown with respect to the third embodiment, the description made with respect to the first or second embodiment is applied, where appropriate.

The topsheet 2 and the backsheet 3 is the disposable diaper 1B according to this third embodiment are extended widthwise outward from longitudinal opposite side edges 41, 41 of the central absorbent core 4, and those extended portions form leg flap portions LF, LF at longitudinal opposite side portions of the diaper. A landing zone 9 for fixing the fastening tapes 5, 5 is disposed at the outer surface of the stomach side region B.

In the disposable diaper 1B according to this third embodiment, a ration (L4/L5) between a smallest width L4 of a crotch region which occupies two inside regions of all four regions which are obtained by dividing the disposable diaper 1B into four equal parts in a longitudinal direction of the diaper and a largest width L5 of the disposable diaper is from 0.4 to 0.8 and more preferably from 0.55 to 0.75. If the ratio (L4/L5) is smaller than 0.4, there occur such inconveniences that (a) the region where the absorbent core is disposed is too small to obtain a sufficient absorption performance and especially when it is tried to form the diaper into the shape of trunks, it becomes difficult to substantially obtain the region where the absorbent core is disposed, and that (b) the lug portion of the side flap is likely to open and flap during conveyance in machining process (deterioration in machining). In contrast, if the ratio is larger than 0.8, deterioration in wearability is unavoidable.

Figure 8:
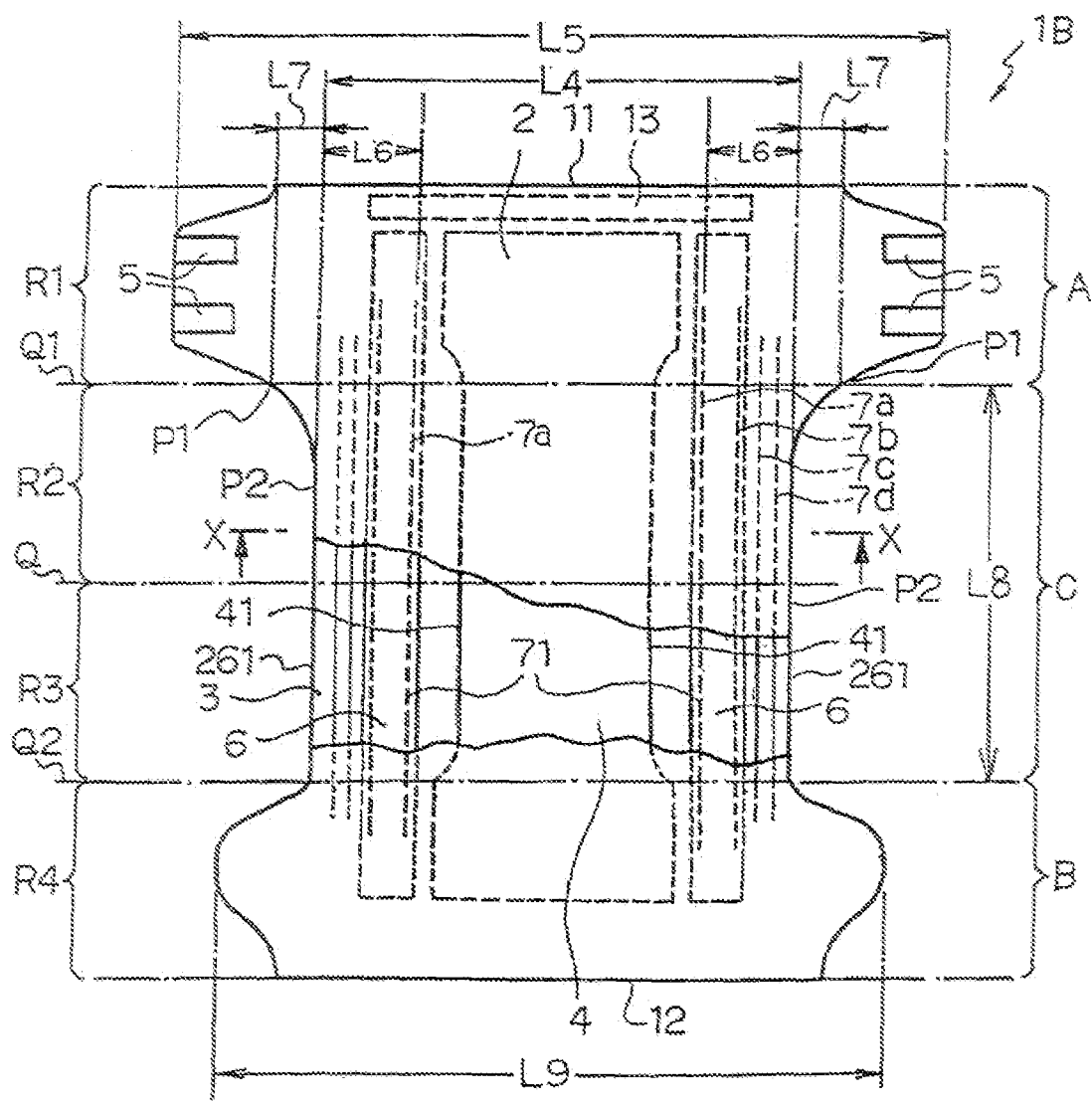
FIG. 8 is a plan view showing, partly cut-away, a disposable diaper according to a further embodiment of the first embodiment.

In FIG. 8, one dot chain lines Q1, Q and Q2 denote lines for longitudinally dividing the disposable diaper 1B into four equal parts. R1 to R4 denote the respective regions obtained by equally dividing the disposable diaper into four parts in a longitudinal direction. The crotch region C is a combination of the region R2 and the region R3. The dimensions of the various portions and the ratios described in this specification are dimensions obtained by measurements carried out in a state (tensioned state) in which the diaper is planarly spread as shown in FIG. 8 and the ratios based thereon unless described otherwise specifically.

In the disposable diaper 1B according to this embodiment, the largest width L5 at the back side region A is preferably larger than the largest width L9 at the stomach side region B from the view point of wearability.

Figure 11:
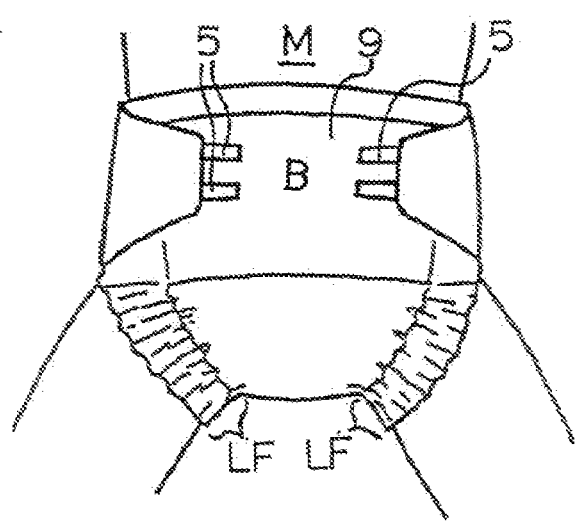
FIG. 11 is a schematic view showing a trunks-like worn state of the disposable diaper of FIG. 8.

In the disposable diaper 1B, a plurality of leg portion elastic members 7a to 7d are disposed at the leg flap portions LF, LF located at the outside areas of the longitudinal opposite side edges 41, 41 of the central absorbent core 4 along a longitudinal direction of the diaper. The ratio (L6/L4) between the shortest distance L6 between the innermost edge 71 of the leg portion elastic member and the outermost edge 261 of the leg flap portion LF and the shortest width L4 of the crotch region C is from 0.1 to 0.25. If the ratio (L6/L4) is within the above-mentioned range, as shown in FIG. 11, that portion, which is located at a widthwise outside area of the inner side edge 71 of the leg portion elastic member in the crotch region C, takes such a shape as to be wound around the wearer's upper thigh portion in a state in which the diaper is applied to the wearer. By this, the distance of the path for the excretions to leak therethrough becomes long and so, the effect of the leak prevention is enhanced. Moreover, the disposable diaper according to this embodiment is design-wise excellent in outer appearance that can give a good impression in terms of leak-preventive property to the wearer, the helper, etc. If the ratio (L6/L4) is smaller than 0.1, the diaper becomes unable to take the shape of trunks. In contrast, if the ratio (LL6/L4) is larger than 0.25, the disposable diaper becomes difficult to put on because the leg flap portion is caught by the wearer's upper thigh portion at the time of putting on the diaper.

The leg portion elastic member used herein refers to the elastic member disposed at the flap portion LF formed on each opposite side portion of the crotch region C along a longitudinal direction of the diaper, and the innermost edge 71 of the leg portion elastic member used herein, refers, in case only one leg portion elastic member is disposed at the leg flap portion, to the inner edge portion of the leg flap portion in a widthwise direction of the diaper, and in case a plurality of leg portion elastic members 7a to 7d are disposed at the leg flap portion as this disposable diaper 1B, to the inner edge portion of the leg portion elastic member 7a, which is, among those leg portion elastic members 7a to 7d, disposed at the innermost side of the diaper, in a widthwise direction of the diaper.

In this disposable diaper 1B, the ratio (L7/L8) between a widthwise distance L7 between an outermost point P1 of the outer edge 261 of the leg flap portion LF and an innermost point P2 thereof in the crotch region C and a longitudinal length L8 of the crotch region C is from 0 to 0.2. If the ratio (L7/L8) is larger than 0.2, the disposable diaper becomes difficult to put on because the leg flap portion is caught by the wearer's upper thigh portion at the time of putting on the diaper.

The outermost point P1 of the outer edge 261 of the leg flap portion LF used herein refers to a point on the outer edge where the distance from a center line (not shown) for dividing the disposable diaper into two equal parts in a widthwise direction of the diaper becomes longest, and the innermost point P2 of the outer edge 261 used herein refers to a point on the outer edge 261 where the distance from the center line becomes shortest. The widthwise distance L7 between the outermost point P1 and the innermost point P2 can be obtained by subtracting the distance from the center line for dividing the disposable diaper into two equal parts in a widthwise direction of the diaper to the innermost point P2 from the distance from the center line to the outermost point P1. The ratio (L7/L8) equals 0 (zero) refers to a case where the outer edge 261 of the leg flap portion LF in the crotch region C defines a linear line in parallel with a longitudinal direction of the diaper over the lengthwise entire area of the crotch region C. A diaper of the above-mentioned form is also included in one preferred embodiment of the present invention.

In the disposable diaper 1B according to the third embodiment, the outermost point P1 of the outer edge 261 of the leg flap portion LF in the crotch region C is located at the back side region (the above regions R1 and R2) of all the two regions obtained by dividing the disposable diaper 1B into two equal parts in a longitudinal direction of the diaper.

In the disposable diaper 1B according to this embodiment, although two pairs of fastening tapes 5, 5 are employed, one pair, or three pairs or more of fastening tapes may be employed. However, in the case where one pair of fastening tapes are employed, it is preferred that the waist portion elastic member 13 for forming the waist gather is disposed along the back side waist edge portion 11 in order to prevent the deterioration of the fitness. At the time of measuring the largest width of the disposable diaper 1B, the measurement is carried out in a state in which the fastening tape 5 is bent inward as shown in FIG. 8.

In the disposable diaper 1B according to this embodiment, the second absorbent cores 6, 6 each having a predetermined width are disposed at least at a part of the leg flap portions LF in the crotch region C. More specifically, the fluid retentive second absorbent cores 6, 6 are disposed at outside areas of opposite side edges 41, 41 of the central absorbent core 4 in the crotch region C in such a manner as to be spaced apart from the opposite side edges 41, 41 respectively. The second absorbent cores 6, 6 each have a belt-like configuration and are disposed along a longitudinal direction of the diaper 1. The second absorbent core 6 is approximately equal in width over its longitudinal direction in the crotch region C and is disposed such that its longitudinal direction is aligned with a longitudinal direction of the diaper 1.

The second absorbent cores 6 may be disposed at least at a part of the leg flap portions Lf. However, since the excretions migrating over the central absorbent core 4 are likely to reach not only the leg flap portions LF, LF in the crotch region C but also the flap portions in the back side and stomach side regions when the diaper wearers excrete urine, etc. while lying on their side, the second absorbent cores 6 are preferably disposed over at least one of the stomach side flap portion (that portion located at an outside area of each opposite left (or right) side edge of the central absorbent core 4 in the stomach side region B) and the back side flap portion (that portion located at an outside area of each opposite left (or right) side edge of the central absorbent core 4 in the back side region A) from the crotch region C, and more preferably disposed over both the stomach side flap portion and the back side flap portion from the crotch region C.

In the disposable diaper of the present invention, the topsheet 2 disposed on the central absorbent core 4 is extended widthwise outward from the opposite side edges of the central absorbent core 4 and the extended portions of the topsheet 2 preferably cover at least the inner edges of the second absorbent cores 6, 6, respectively, and in order to prevent the fluid from oozing out from the second absorbent cores 6, 6 the outer edges of the second absorbent core 6 is preferably covered with a fluid-impermeable sheet.

According to the disposable diaper 1B of the third embodiment, since the ratios (L4/L5), (L6/L4) and (L7/L8) are within the above-mentioned specific ranges, respectively, the diaper can take the trunks-like shape, as shown in FIG. 11, during wearing the diaper. Thus, the leak preventing effect and design can be enhanced. Moreover, there is no such an inconvenience that the diaper is difficult to put on or apply as often experienced in the conventional trunks-like diaper.

In the disposable diaper 1B according to the third embodiment, since the leg portion elastic members 7a, 7b are not disposed at the regions F between the central absorbent core 4 and the second absorbent cores 6, 6, the shrinking force of the leg portion elastic members disposed at the widthwise outside areas of the regions F is absorbed and damped by the regions F. Accordingly, this absorbent diaper is excellent in fit, absorbent performance, and in pad storability in case an absorption pad is used in combination.

From the view point of exhibiting the enhancement of fitness and the effect of leak prevention more significantly, the width L3 of each second absorbent core 6 is preferably from 1 to 10 cm and particularly preferably from 2 to 5 cm, and the ratio (L3/L4) between the width L3 an the smallest width L4 of the crotch region C is preferably from 0.02 to 0.3. Also, the width L1 of the central absorbent core 4 is preferably from 5 to 25 cm, and the ratio (L1/L4) between the width L1 and the smallest width L4 of the crotch region C is preferably from 0.1 to 0.8.

The layer structure of the leg flap portion is not limited to those of the above-mentioned embodiment. For example, instead of the topsheet 2 and/or backsheet 3, the layer structure of the leg flap portion may be constituted of a single or a plurality of other sheets, or besides the topsheet and backsheet 2, 3, other sheets and non-sheets may be employed.

As a method for forming the central absorbent core and the second absorbent core in the first invention, there can be considered (a) the central absorbent core and the second absorbent core are supplied as separate bodies, (b) a slit is formed in or an emboss is formed on the central absorbent core over its entire length or at least at the crotch region in a longitudinal direction thereof, (c) a region having a small weight per unit area is formed at the central absorbent core over its entire length or at least at the crotch region in a longitudinal direction thereof, (d) the widthwise opposite end portions of absorption materials having a wide width are folded back towards the surface facing the inner surface side of the diaper and laminated, and then, absorption materials having a narrow width are laminated on a central portion between the two laminated portions so that a prescribed gap is formed between the inner edge portions of the laminated portions and the a absorption materials, and the like.

Another preferred embodiment of the first invention includes a diaper having the central absorbent core 4 and the second absorbent cores 6, 6 which are integrally connected with each other and segmented by an embossing line formed along the longitudinal direction of the diaper.

When the central absorbent core and the second absorbent core are formed in the manner as mentioned above, the regions F become bent regions and the second absorbent core is surely bent towards the upper thigh, thereby enhancing the fitness at the crotch upper thigh portion, leak-preventive property and trunks-like outer appearance. In the above (d) method, the portion composed of the two-layer absorption materials formed on the central portion constitutes the central absorbent core, and the portion composed of the two-layer absorption materials constitutes the second absorbent core.

Preferred embodiments of the second invention will be described hereinafter. A disposable diaper 1C as one embodiment of the second invention has, as shown in FIGS. 12 to 15, the same basic construction as the above-mentioned disposable diaper 1B. Accordingly, like components are denoted by like reference numerals and description thereof is omitted. About those points which are not particularly described, the description made with respect to the disposable diaper 1B is applied, where appropriate.

In the disposable diaper 1C of the second invention, the second absorbent cores 6, 6 are disposed at the outside areas of the opposite side edges 41, 41 of the central absorbent core 4 in the crotch region C along a longitudinal direction of the diaper. The second absorbent cores 6, 6 according to this embodiment are disposed in such a manner as to be spaced apart from the opposite side edges 41, 41 of the central absorbent core 4. They are in the form of belt and are fixedly sandwichingly held between the topsheet 2 and the backsheet 3 extending widthwise outward from the opposite side edges in a longitudinal direction of the central absorbent core 4 such that their longitudinal direction is aligned with the longitudinal direction of the diaper.

In this second invention, although it suffices that the second absorbent cores 6 are provided to at least one part in the longitudinal direction in the crotch region C, they are preferably disposed from the crotch region C over to at least one of the back side region A and the stomach side region B. It is more preferable that the second absorbent cores 6 are disposed from the crotch region C over to both the back side region A and the stomach side region B as in this embodiment.

Figure 12:
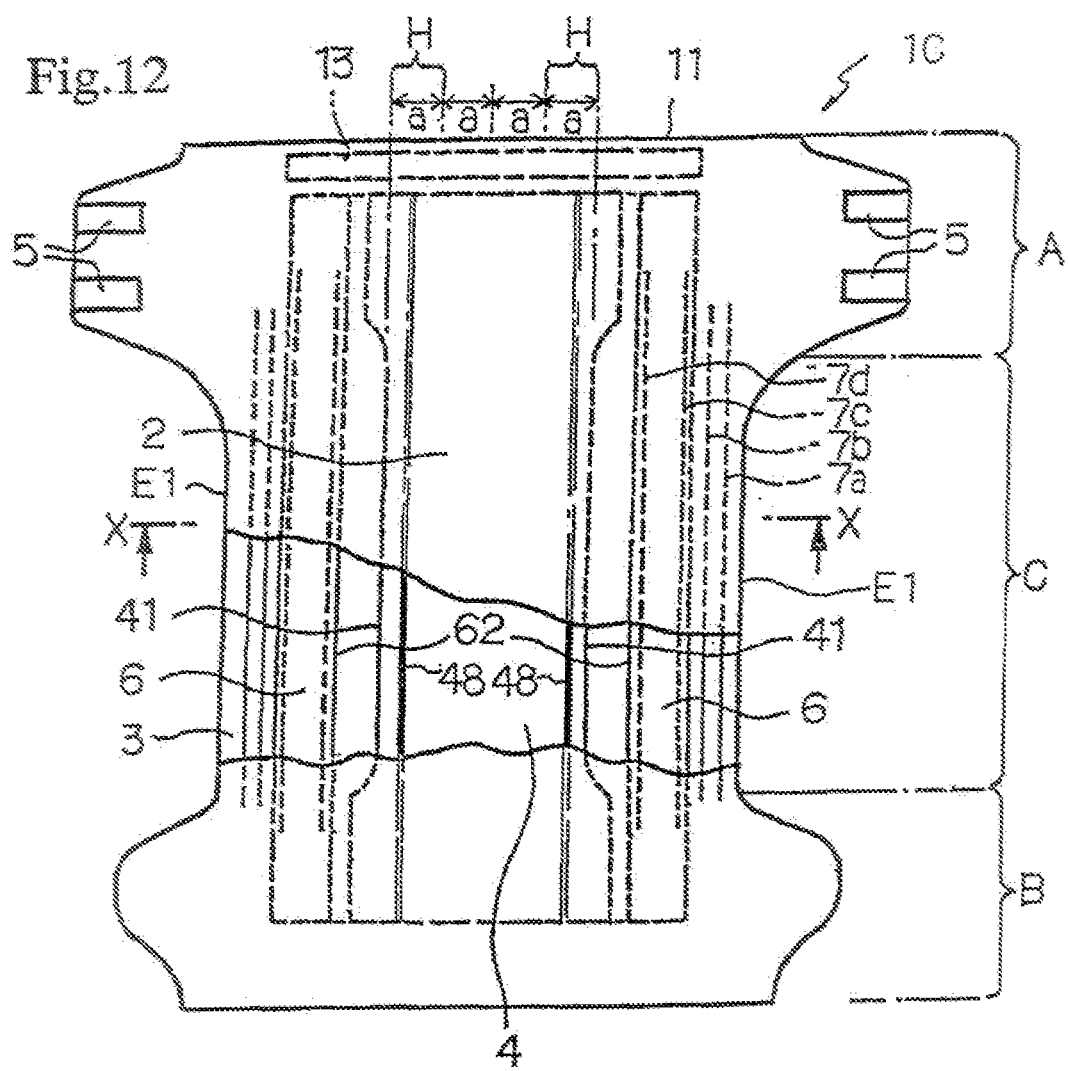
FIG. 12 is a plan view showing, partly cut-away, a disposable diaper according to one embodiment of the second invention.
Figure 13:
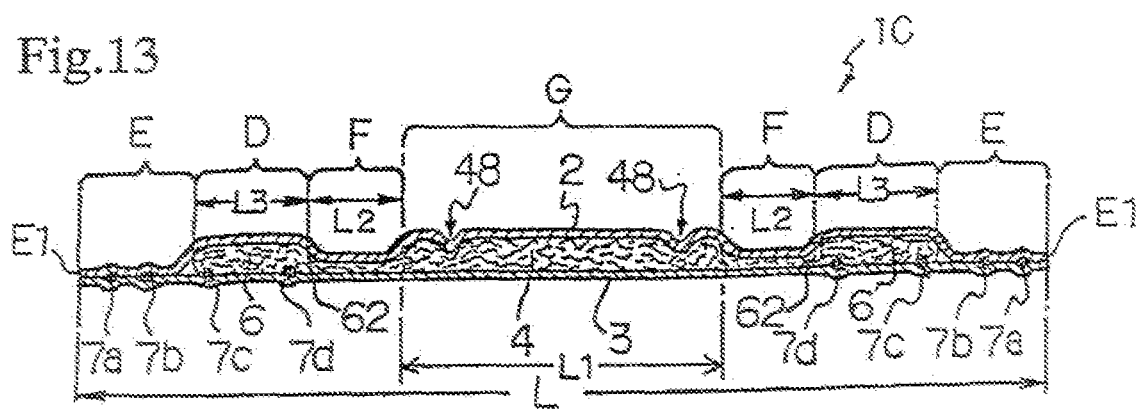
FIG. 13 is a schematic sectional view taken on line X-X of FIG. 12.

In the disposable diaper 1C of the second invention, the basis weights (basis weights of the absorbent core per unit area) in the intermediate regions F, F located between the central absorbent core 4 and the second absorbent cores 6, respectively are smaller than the basis weights of the absorbent cores in the region G where the central absorbent core 4 is disposed and in the regions D where the second absorbent cores 6 are disposed. The basis weight of the intermediate regions F may be 0 (zero). The region G where the central absorbent core 4 is disposed and the regions D where the second absorbent cores 6 are disposed, used herein refer to those regions where the central absorbent core 4 or the second absorbent cores 6 are disposed at the interior of the disposable diaper in a thickness direction, when the diaper is plan viewed in a tensioned state (the state in which the elastic members at various portions are stretched and planarly spread) as shown in FIG. 12.

The basis weight per unit area of the region G where the central absorbent core 4 is disposed, the basis weight of the absorbent cores in the regions D where the second absorbent cores 6 are disposed, and the basis weight per unit of the absorbent cores in the intermediate regions F located between the central absorbent core and the second absorbent cores can be obtained as follows, respectively. Test pieces of 1 cm×1 cm are cut out from the regions G, D, F, respectively. Then, the weights of the test pieces are measured and converted into basis weights ($g/cm^2$). In this invention, the "absorbent core" refers to a layer adapted to absorb/retain fluid, such as water absorption polymer, pulp and mount, and it does not include the topsheet 2 and the backsheet 3. Accordingly, in the case where the intermediate regions F are composed of only the topsheet 2 and the backsheet 3, the basis weight of the absorptive cores in the intermediate region is 0 (zero).

In the disposable diaper 1C of the second invention, one pair of axes of flexibility 48, 48 serving as bent portions (bend lines) at the time of bending the central absorbent core in the widthwise direction, are formed on the opposite side portions of the absorbent, core 4 at least at one part of the diaper in the longitudinal direction, along the longitudinal direction of the central absorbent core 4.

In this invention, the pair of axes of flexibility 48, 48 may be formed on the central absorbent core 4 in the crotch region C or on the central absorbent core 4 in the back side region A and/or stomach side region B. The pair of axes of flexibility 48, 48 are preferably formed from the crotch region C over to the back side region A and/or stomach side region B, and more preferably formed all over the back side region A, the crotch region C and the stomach side region B.

Figure 15:
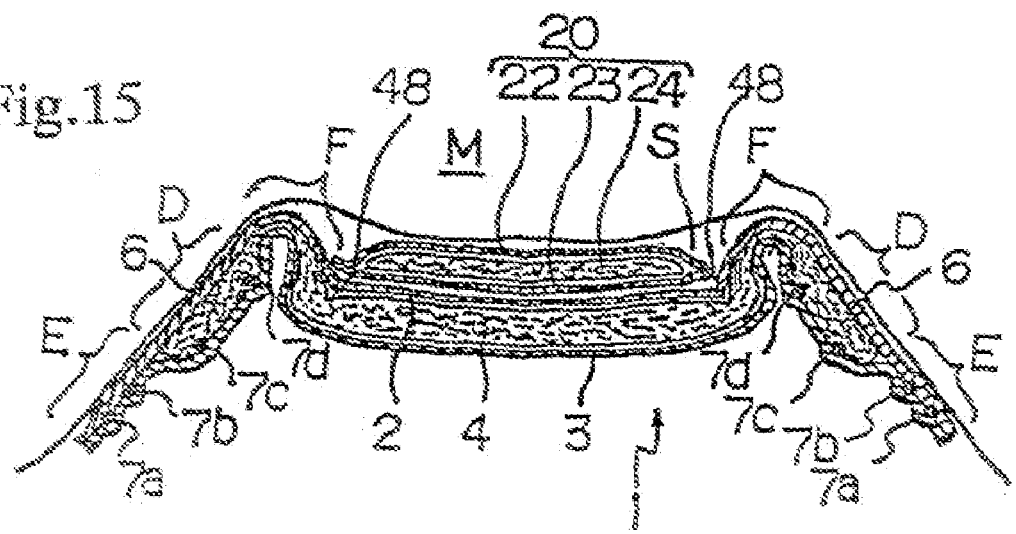
FIG. 15 is a schematic sectional view showing a using state of the disposable diaper of FIG. 12.

In the case where the axes of flexibility 48, 48 are disposed at the central absorbent core 4 in the crotch region C, the opposite side edge portions of the central absorbent core 4 are easily stood up along the axes of flexibility 48, 48 and the central absorbent core 4 is formed into a recessed shape as shown in FIG. 15. Moreover, since the opposite side edge portions of the central absorbent core 4 having a large basis weight are stood up, the intermediate regions F having a smaller basis weight than the region G where the central absorbent core 4 is disposed, are also easily stood up. Since the opposite side edge portions of the central absorbent core 4 which are stood up as mentioned above and the intermediate regions F connected thereto are functioned as a leak-preventive barrier (three-dimensional barrier), there can be obtained a disposable diaper having an excellent leak-preventive property.

Moreover, since the opposite side edge portions of the central absorbent core 4 and the intermediate regions F are stood up, recessed pockets S capable of stably retaining an auxiliary absorber 20 such as an auxiliary pad, are formed on the inner surface of the disposable diaper 1C. Accordingly, the storability/retainability of the auxiliary absorber 20 can be enhanced in the case where the auxiliary absorber 20 is disposed on the inner surface of the disposable diaper 1C and used in combination. By this, even in the case of the auxiliary absorber 20 having no fixing means, no positional displacement occurs during wearing the diaper. Moreover, the arrangement or replacement of the auxiliary absorber 20 can be carried out very easily and rapidly. The auxiliary absorber 20 shown in FIG. 15 is an absorptive pad having the above-mentioned construction and is disposed within the pocket S with its longitudinal direction aligned with the longitudinal direction of the disposable diaper 1C. Moreover, since the basis weight of the absorbent cores at the regions D where the second absorbent cores are disposed, is larger than the basis weight of the absorbent cores in the intermediate regions F, the second absorbent cores are bent outwardly in the widthwise direction and there occurs no such inconvenience that the second absorbent cores are fallen towards the inner side at the time of putting on the diaper.

In the case where the axes of flexibility 48, 48 are disposed at the central absorbent core 4 in the crotch region C, it is preferred that the axes of flexibility 48, 48 are formed at least at the central portion of the crotch region C and their length in the longitudinal direction is 50% or more, and particularly 80% or more based on the entire length of the crotch region C in the longitudinal direction. In the case where the axes of flexibility 48, 48 are not disposed at the central absorbent core 4, the standability of the intermediate regions F, F are lowered and the formability of the leak-preventive barrier is lowered. If the basis weight of the absorbent cores in the intermediate regions F, F is larger than the basis weight of the absorbent core in the region G where the central absorbent core 4 is disposed, the standing up of the side edge portions of the central absorbent core is jeopardized, and the formation of the pocket by the central absorbent core and the formation of the leak-preventive barriers at the intermediate regions is jeopardized.

In the case where the pair of axes of flexibility 48, 48 are formed at the central absorbent core 4 in the back side region A and/or stomach side region B, the back side region A and/or the stomach side region B of the diaper are brought into a curved configuration so as to be nice fit to the wearer's body contour at the time of putting on the diaper, and therefore, the diaper is very easy to put on or apply. In the disposable diaper according to this embodiment, the pair of axes of flexibility 48, 48 are formed all over the back side region A, the crotch region C and the stomach side region B, and the respective axes of flexibility 48 are formed on the central core 4 over the lengthwise entire area thereof.

The axes of flexibility of the second invention may be properly selected from those in which in a state (natural state) where no external force is exerted to the diaper, the central absorbent core is bent at the axes of flexibility and the opposite side edge portions of the central absorbent core are located at an upper position than the central portion in a widthwise direction of the central absorbent core. As a method for forming them, there can be listed (a) a part of the central absorbent core is compressed and the compressed part of the central absorbent core serves as the axes of flexibility, (b) a part of the central absorbent core is melted by heat treatment and the melted portion serves as the axes of flexability, (c) a slit is formed in the central absorbent core over a widthwise entire area thereof or a cut is formed in the central absorbent core at only a part of the widthwise entire area thereof, and that portion where the slit or cut is formed serves as the axes of flexibility, (d) the central absorbent core is folded back to bond the outer surface sheets together and the portion bent at that time serves as the axes of flexibility, (e) regions each having a different rigidity (different in basis weight, or the like) are disposed in a widthwise direction of the absorbent core and the borderline between the different rigidities serves as the axes of flexibility, and the like.

The axes of flexibility 48, 48 in the disposable diaper 1C according to this embodiment are formed by folding back the opposite side edge portions of the central absorbent core 4 towards the inner surface side of the diaper along a longitudinal direction of the diaper and the bent portion is compressed by embossing, pressing machine or the like. Prior to this compressing treatment, emboss treatment is applied to at least a part of the central absorbent core along its longitudinal direction or a hot melt type adhesive agent is applied to preliminarily harden that part of the central absorbent core so that at least a part of the bending portion occupies the hardened portion. By doing so, the formability, retainability of the axes of flexability are further enhanced.

The axes of flexibility are formed at a position of preferably from 5 to 70 mm and more preferably from 5 to 50 mm from the side edges 41 of the central absorbent core 4 inward over the longitudinal entire length. The basis weight of the region G where the central absorbent core 4 including the axes of flexibility are disposed is preferably 550 g/m$^2$ or smaller and more preferably 300 g/m$^2$. If the basis weight of the region G is 300 g/m2 or smaller, the opposite side edge portions of the central absorbent core 4 are easy to carry out and the restoring force is reduced. Accordingly, a folded-back shape (the shape bent at the axes of flexibility) is easily retained on the central absorbent core. If the basis weight of the absorbent core 4 including the axis of flexibility portion is 550 g/m$^2$ or smaller, the axes of flexibility are easy to form and the folded-back shape is easy to retain. Accordingly, the formability of the leak-preventive barrier is enhanced.

In the disposable diaper of the second invention, the central absorbent core 4 and the second absorbent cores 6, 6 may be separate bodies. However, it is preferred from the view point of simplicity of machining process that the central absorbent core 4 and the second absorbent cores 6, 6 are integrally formed. In this case, the boundaries between the intermediate region F and the regions C and D are established as follows.

In the case where the basis weight of the absorbent core is abruptly changed in its widthwise direction (same direction as the widthwise direction of the diaper), the boundaries between the absorbent cores of the intermediate regions and the central absorbent core and second absorbent cores are the line extending along the longitudinal direction where the basis weight of the absorbent core is clearly changed in the widthwise direction. In the case where the basis weight of the absorbent core is gently changed in its widthwise direction (same as the widthwise direction of the diaper), the boundaries between the absorbent cores in the intermediate regions and the central absorbent core are the line passing through the widthwise center between the line where the basis weight along the longitudinal direction is smallest (when the portions having the same basis weight exist over a plane, the line closest to the inner edge) and the line (when the portions having the same basis weight exist over the plane, the line closest to the outer edge) on the central absorbent core 4 where the basis weight is largest, while the boundaries between the absorbent cores in the intermediate regions and the second absorbent cores are the line passing through the widthwise center between the line where the basis weight is smallest (when the portions having the same basis weight exist over a plane, the line closest to the outer edge) and the line (when the portions having the same basis weight exists over a plane, the line closest to the inner edge). The regions having a prescribed width sandwiched between two boundaries established in this way serve as the intermediate region.

In the second invention, the ratio (the former/the latter) between the basis weight of the absorbent cores in the intermediate region F and the basis of the absorbent core in the region G where the central absorbent core 4 is disposed is preferably from 0 to 0.5. Also, the ratio (the former/the latter) between the basis weight of the absorbent cores in the intermediate regions F and the basis weight of the absorbent cores in the regions D where the second absorbent cores 6 are disposed is preferably from 0 to 0.5. The difference of the basis weights of the absorbent cores between the region G and the intermediate regions F and the difference of the basis weights of the absorbent cores between the regions D and the intermediate regions F are preferably at least 100 g/m$^2$ or larger and particularly preferably 200 g/m$^2$ or larger.

In the disposable diaper of the second invention, elastic members are disposed along a longitudinal direction of the diaper at the regions D where the second absorbent cores 6 are disposed and/or at edge flap portions E which are formed at widthwise outside areas of the regions where the second absorbent cores 6 are disposed and where no absorbent cores exist, and the basis weight of the absorbent cores in the intermediate regions F is preferably ⅔ or smaller the basis weight of the absorbent cores in the regions D where the second absorbent cores 6 are disposed.

Two elastic members 7a, 7b are disposed at each edge flap portion E in the disposable diaper 1C according to this embodiment, and two elastic members 7c, 7d are disposed at each region D where the second absorbent core 6 is disposed.

In the disposable diaper 1C according to this embodiment, since the elastic members 7c, 7d are disposed along a longitudinal direction of the diaper at each region D where the second absorbent core 6 is disposed, the skin side surface of the region D nicely fits around the leg area of the wearer M as shown in FIG. 15. Accordingly, even if urine, etc. should leak out to the side of the central absorbent core 4, they are surely captured by the second absorbent cores 6 without being allowed to reach the side edge portions of the diaper. Moreover, since the elastic members 7a, 7b are also disposed at the edge flap portions E which are located at the outside areas thereof, duplex leak-preventive means is formed at the crotch region and thus, leak of excretions occurrable from the crotch region can more surely be prevented.

In the case where the elastic members 7c, 7d are disposed at each region D where the second absorbent core is disposed and the basis weight of the absorbent cores in the intermediate regions F is set to ⅔ or less the basis weight of the absorbent cores in the regions D where the second absorbent cores 6 are disposed, the intermediate regions are easily stood up to form the leak-preventive barrier by the shrinking force occurrable when the second absorbent cores 6, 6 and/or the leg flap portions E are shrunk. Accordingly, the storability/retainability of the auxiliary pad, etc. and the leak-preventive property are enhanced extensively. In the case where the basis weight of the absorbent cores in the intermediate regions F and the basis weight of the absorbent cores in the regions where the second absorbent cores 6 are disposed have the above-mentioned relationship, the regions D where the second absorbent cores 6 are disposed are surely bent outward by the weight difference. Accordingly, there can surely be prevented such an inconvenience that the regions D are fallen towards the inner side at the time of putting on the diaper. The basis weight of the absorbent cores in the intermediate regions is preferably ½₀ or more the basis weight of the absorbent cores of the regions D where the second absorbent cores 6 are disposed.

In the disposable diaper 1C according to this embodiment, as shown in FIG. 12, the axes of flexibility 48, 48 are formed at the outer two regions H, H of all the four regions obtained by dividing the central absorbent core 4 into four equal parts in a widthwise direction. Owing to this construction, even in the case where the opposite side edge portions of the central absorbent core 4 are completely folded back onto the inner surface of the diaper along the axes of flexibility 48, 48 it never happens that the inner surface of the region G where the central absorbent core 4 is disposed is blocked with the folded-back portion because the opposite side edge portions of the central absorbent core 4 are not overlapped with each other. Thus, the problem of lowering of the absorptive performance does not occur. Moreover, by preventing the side edge portions of the central absorbent core from being overlapped with each other, the pack volume can be reduced at the time of compression charging the diaper into a packing bag for packing.

The axes of flexibility 48, 48 of the disposable diaper 1C according to this embodiment is formed by folding back the opposite side edge portions 41, 41 of the central absorbent core 4 towards the inner surface side of the diaper along a longitudinal direction of the central absorbent core 4 and compressing the folded back portions. The axes of flexibility 48, 48 are formed over the entire length in the longitudinal direction of the central absorbent core 4. By this, the axes of flexibility can be formed over the entire length of the central absorbent core 4 easily and without a need of extensive reconstruction of the conventional equipment. Moreover, the manufacturing cost can be reduced.

In the disposable diaper of the second invention, the shrinkage in a longitudinal direction of the edge flap portions E in the crotch region C in the longitudinal opposite left and right sides is preferably larger than the shrinkage in a longitudinal direction of the regions (leg absorbent portions) D where the second absorbent cores 6 are disposed. The longitudinal shrinkages of the edge flap portion E and the regions (leg absorbent portions) D where the second absorbent cores 6 are disposed are measured by the above-mentioned method.

Preferred ranges of the shrinkage Q at the leg absorbent portion D (leg absorbent portion) provided with the second absorbent core 6, the shrinkage P at the edge flap portion E and the ratio (P/Q) are the same as those of the disposable diaper 1A from the same view points as those.

Figure 14:
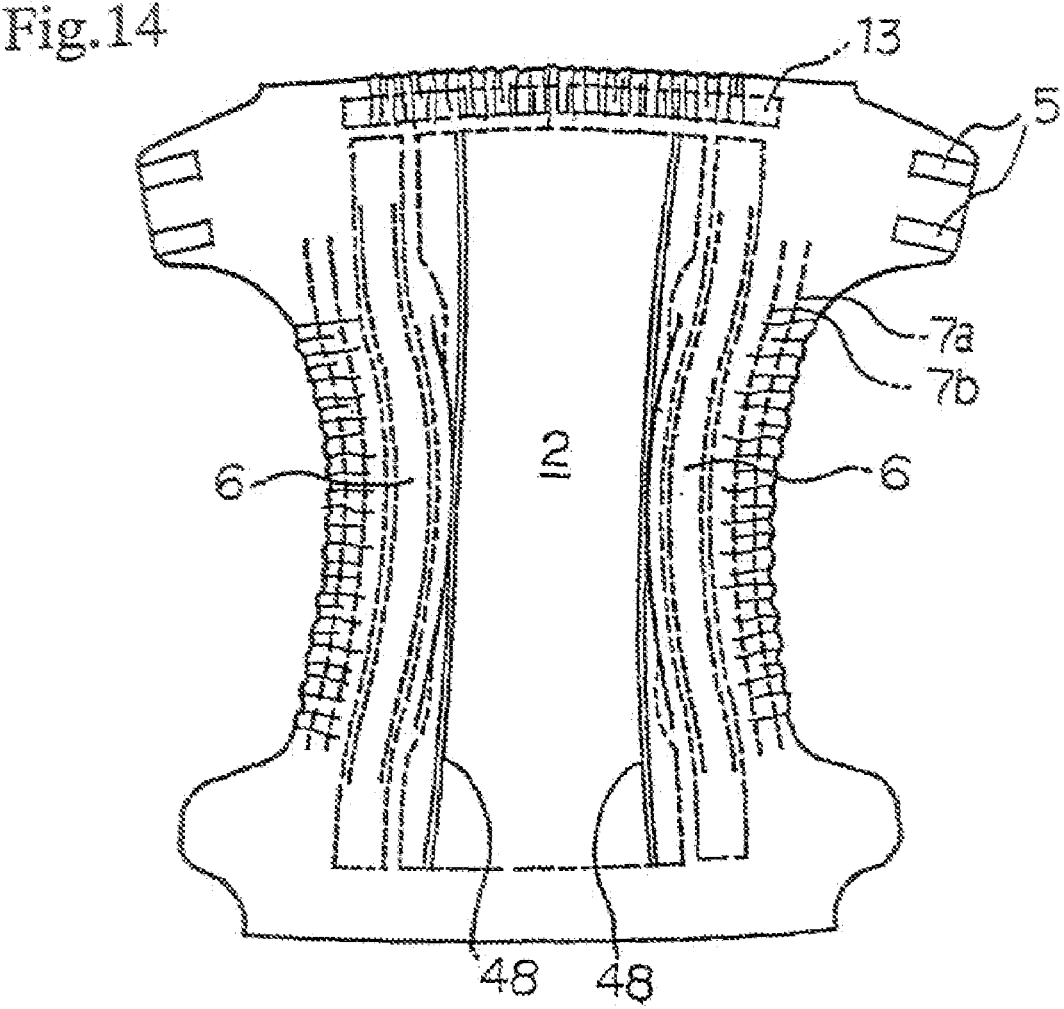
FIG. 14 is a plan view (bird's eye view) showing a natural state of the disposable diaper of FIG. 12 in which its topsheet side (that surface side facing the wearer's skin) faces upward.

By making the shrinkage in the longitudinal direction of the edge flap portion E in the crotch region C larger than the shrinkage in the longitudinal direction of the region D where the second absorbent core 6 is disposed, the second absorbent cores 6, 6 in the crotch region C are, in a natural state, protuberatingly curved widthwise inwards of the disposable diaper easily and surely without losing the shrinking force of the elastic members 7a, 7b disposed at the edge flap portion E by shrinkage of the region D where the second absorbent core 6 is disposed (see FIG. 14). Owing to this construction, the disposable diaper according to this embodiment is more excellent in leak-preventive property, storability/retainability of the auxiliary absorber and also excellent in the fitness at the crotch portion. The first and second inventions can be applied to a shorts type diaper, too. In that case, the side seal portions at the opposite side portions of the diaper are peeled off and the diaper is then developed. The shrinkage, dimensions, etc. of the various portions are measured in that state, and the curved condition of the second absorbent cores is determined in a natural state.

From the view point of exhibiting at least one of the above-mentioned effects efficiently, the width of each portion and the ratio of the width of each portion in the crotch region C of the disposable diaper 1C are preferably same as the above-mentioned disposable diapers 1, 1A.

The first and second inventions are not limited to the above-mentioned various embodiments and they can be changed and modified in accordance with necessity and without departing from the gist of each invention. For example, as one form of arrangement of the second absorbent cores 6, the central absorbent core 4 and the second absorbent cored 6 may be arrange adjacent to each other through a slit and without being spaced apart from each other, or the second absorbent cores 6 may be integrally connected to the central absorbent core 4 in the back side region A and/or stomach side region B. The second-mentioned form is excellent from the view point of further enhancement of the leak-preventive property in the back side region A and/or stomach side region B.

It is preferred for the reason of simplification of the machining process that the central absorbent core and the second absorbent cores are integrally formed. As a method for integrally forming the central absorbent core and the second absorbent cores, it is preferred that the central absorbent core, the shrinking force damping region and the second absorbent cores are simultaneously formed by (a) applying a low density region in a widthwise direction, (b) a slit or the like is formed in the longitudinal direction, and (c) an absorbent core having a small width is laminated on an absorbent core having a large width at a widthwise center thereof and opposite side edge portions of the large width absorbent core are folded back towards the surface of the large width absorbent core on which the small width absorbent core is laminated, so that a predetermined gap is formed between the opposite side edge portions of the small width absorbent core and the opposite side edge portions of the large width absorbent core.

The central absorbent core and/or the second absorbent cores are preferably applied thereon with an emboss which is either parallel to or slanted to the longitudinal direction of the respective absorbent cores. By applying the emboss to those absorbent cores, the absorbent cores can be used efficiently because the absorbent cores can be prevented from being twisted and fluid such as urine, etc. are dispersed in the longitudinal direction along the line of the emboss.

The outer edges of the second absorbent cores are preferably covered with a water-repellent sheet in order to prevent urine, etc. from leaking out from the outer edges of the second absorbent cores. Moreover, a three-dimensional gather may be arranged for the purpose of the enhancement of the effect of leak prevention. The position for arranging the three-dimensional gather is not particularly limited. It is preferred that a fixing end is formed on the central absorbent core 4 and the sheet material extended more outward in a widthwise direction of the diaper than the fixing end and adapted to form the three-dimensional gather does not overlie the second absorbent core. It is more preferred that the sheet material does not cover the outer edge of the central absorbent core. In this invention, since the leak-preventive barrier is formed by the leg absorbent portions being curved and bulged, it is not particularly necessary to provide the three-dimensional gather. In the case where the three-dimensional gather is provided, a fluid-permeable and fluid-impermeable material can be used. In order to prevent the reduction of the hydrophilic region at the fixing portion, etc., it is preferred that a fluid-permeable material is used.

Also, it is preferred that a color(s) is applied to the region (leg absorbent portion) D where the second absorbent core is disposed, and/or an area in the vicinity of the region D along the longitudinal direction, so that those regions can visually be discriminated form the central region sandwiched between the two colored regions. In contrast, the central region may be colored. By this, much labor required for positioning at the time of putting on the diaper and for positioning the auxiliary absorber for wearing can be improved extensively. As a coloring method, there can b e listed, for example, (a) the opposite sides of the topsheet are colored, (b) the opposite side portions of an upper layer mount of the absorbent core are colored, (c) a lower layer mount of the absorbent core is colored and then, the opposite side portions of the mount are folded back towards the outer surface side, and the like. The disposable diaper of this invention is especially suited to be used as a diaper for an adult person. Also, it can be used without a need of a combined use of the auxiliary absorber. Moreover, the disposable diaper of this invention may be an auxiliary absorber.

No elastic members may be disposed at the region D where the second absorbent core 6 is disposed and/or the edge flap portions E in the second invention. The number of the elastic members disposed at the leg absorbent portions D and/or the edging flap portions E, may be only one, or three or more. The shape, dimensions, forming material, etc. of the various portions of the disposable diaper can be changed in accordance with necessary.

According to the second invention, there can be provided a disposable diaper which is excellent in leak-preventive property and storability/retainability of the auxiliary absorber. Also, according to the second invention, there can be provided a disposable diaper in which the diaper takes a curved configuration nicely fitting to the wearer's body contour and which is very easy to put on or apply.

Figure 16:
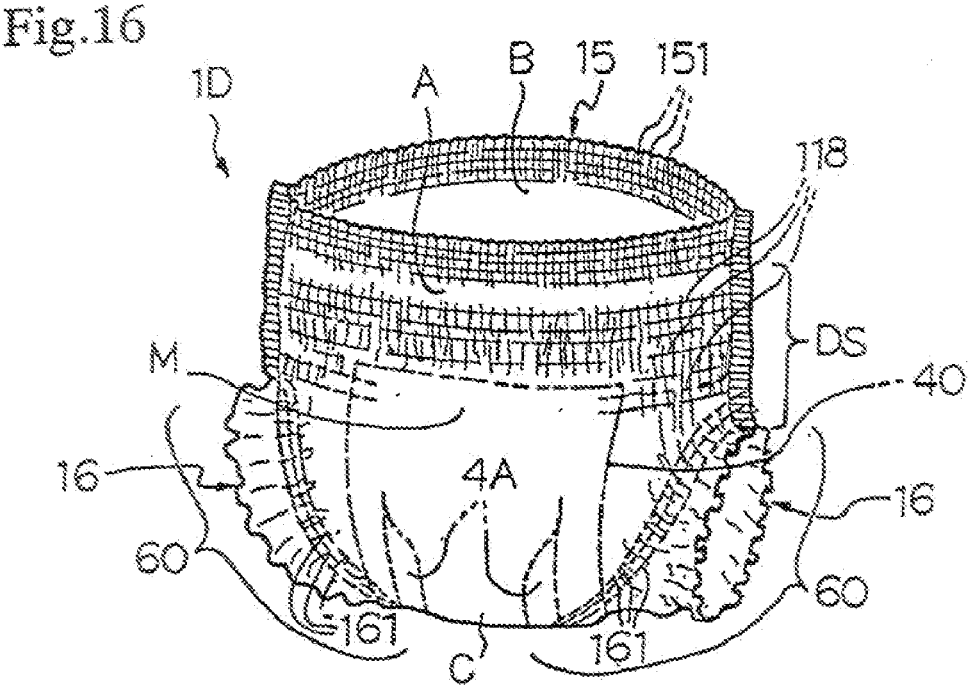
FIG. 16 is a perspective view showing a disposable diaper according to one embodiment of the third invention.
Figure 17:
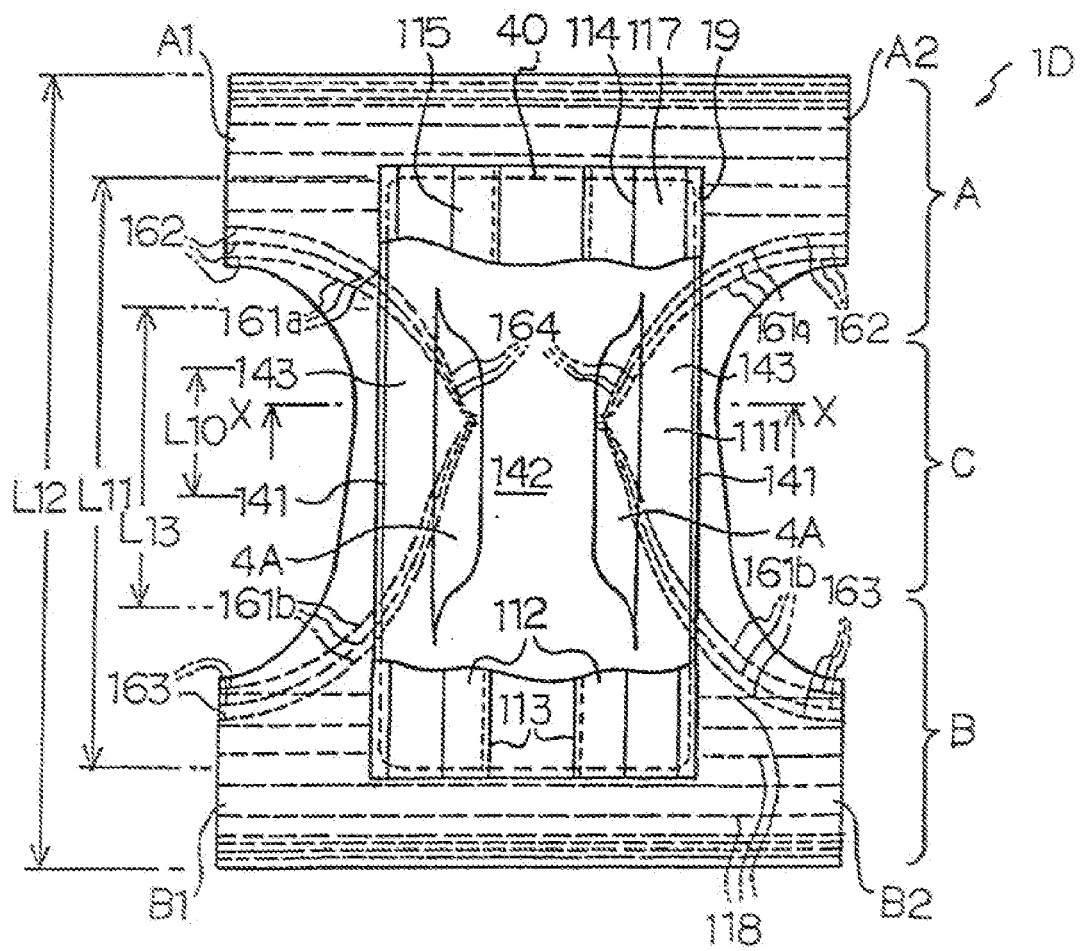
FIG. 17 is a partly cut-out plan view showing a developed state of the disposable diaper of FIG. 16.
Figure 18:
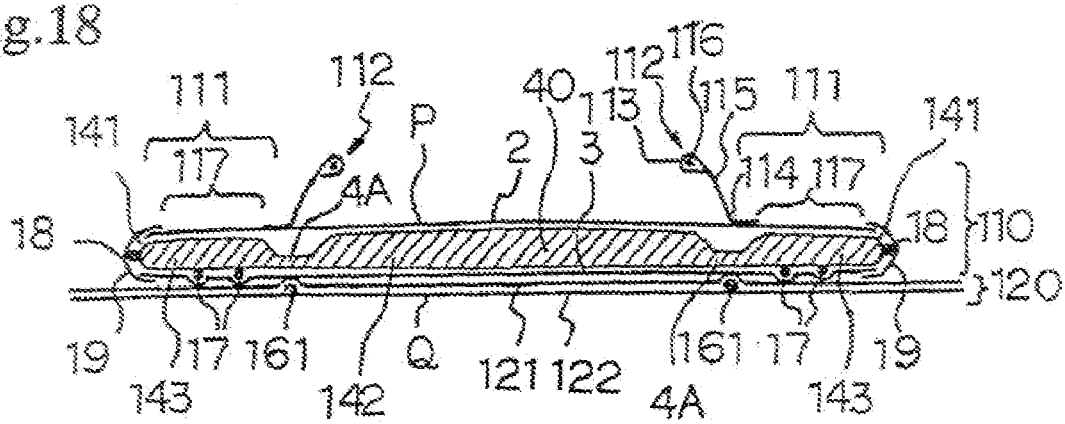
FIG. 18 is a schematic sectional view taken on line X-X of FIG. 17.

Preferred embodiments of the third invention will be described hereinafter. A disposable diaper 1D as one embodiment of the third invention is a shorts type disposable diaper. As shown in FIGS. 16 to 18, the disposable diaper 1D comprises an absorbent main body 110 including a fluid-permeable topsheet 2, a fluid-impermeable backsheet 3 and a fluid-retentive absorbent core 40 interposed between the topsheet 2 and the backsheet 3, and an outer layer body 120 located at an outside area (outer surface side of the diaper) of the absorbent main body 110 and to which the absorbent main body 110 is fixedly joined. Opposite side edges A1, A2 of a stomach side region A which is arranged on the wearer's stomach side at the time of putting on the diaper and opposite side edges B1, B2 of a back side region B which is arranged on the wearer's back side at the time of putting on the diaper are joined together by known joining means such as heat sealing, high frequency sealing, ultrasonic sealing and the like, thereby forming a waist opening portion 15 and one pair of leg opening portions 16, 16.

The absorbent main body 110 has a vertically elongated square configuration. The absorbent main body 110 is joined to a widthwise central portion of the outer layer body 120 with its longitudinal direction aligned with a direction (up and down direction of FIG. 17, hereinafter sometimes referred to as the "longitudinal direction" of the diaper) for connecting the stomach side region A and the back side region B of the disposable diaper 1D which is in a developed state. The absorbent core 40 has an outer contour of a vertically elongated square configuration which is generally same as the absorbent main body 110, and is fixedly sandwiched between the topsheet 2 and the backsheet 3.

A plurality of waist elastic members 151 for forming a waist gather are arranged at predetermined intervals along an opening edge portion thereof, and a substantially continuous annular waist gather is formed over an entire circumference of the waist opening portion 15.

A leg portion elastic member 161 for forming leg gather is disposed in its stretched state on each of one pair of leg portions 60, 60 arranged around the wearer's leg area. Each leg portion elastic member 161 comprises a first elastic member 161a disposed over the crotch region C from the stomach side region A and a second elastic member 161b disposed over the back side region B from the crotch region C. The first elastic member 161a and the second elastic member 161b are overlapped with each other at the crotch region C and function substantially same as a continuous elastic member.

The absorbent core 40 at the diaper crotch region (region disposed at the wearer's crotch in wearing) C is sectioned at least at one part of its longitudinal direction (same direction as the longitudinal direction of the diaper) into one pair of second absorbent cores 143, 143 which are located at widthwise outside areas of the locations of the leg portion elastic members 161 and a central absorbent core 142 which is located between the pair of second absorbent cores 143, 143, by the leg portion elastic members 161, 161. The central absorbent core 142 is located at a widthwise center of the diaper crotch region C, while the second absorbent cores 143, 143 are located at opposite left and right sides of the central absorbent core 142.

Figure 19:
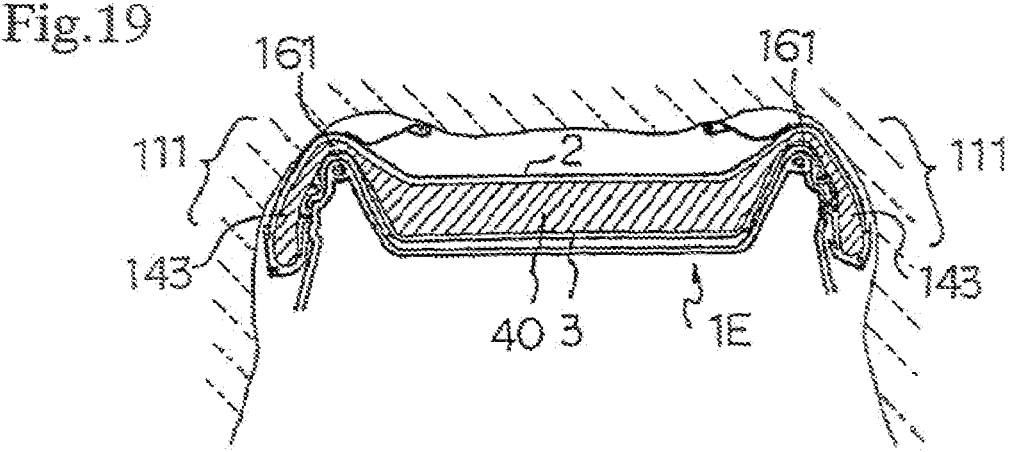
FIG. 19 is a schematic view showing a worn state of the disposable diaper of FIG. 16.

In this embodiment, the absorbent core 40 at the diaper crotch region C includes one pair of low rigidity regions 4A, 4A which are spaced apart from the opposite left and right side edges 141, 141 in a longitudinal direction of the absorbent core 40 and which are lower in rigidity than other parts. The pair of low rigidity regions 4A, 4A are formed along the longitudinal direction of the absorbent core 40. The second absorbent core 143 sectioned by the leg portion elastic member 161 is bent at its topsheet 2 side outward in a widthwise direction of the diaper by the elastic shrinking force of the leg portion elastic member 161 at the time of putting on the diaper. That is, as shown in FIG. 19, the second absorbent core 143 is bent towards the backsheet 3 side serving the part of arrangement of the leg portion elastic member 161 as a bending line. By this, since the fluid-retentive absorbent core is disposed along the leg part of the wearer, the leak-preventive property is high compared with the conventional one.

The leg portion elastic member 161 is, as shown in FIG. 17, disposed in such a manner as to be curved in a generally arc shape. One end portion 162 of each leg portion elastic member 161 located on the stomach region A side and the other end portion 163 located on the back side region B are located at the widthwise outside areas of the side edge of the absorbent core 40. A central part 164 of each leg portion elastic member 161 passes a widthwise inside area of the side edge 141 of the absorbent core 40 in the diaper crotch region C. More specifically, the central part 164 of each leg portion elastic member 161 passes the low rigidity region 4A. The expression "the central part 164 of each leg portion elastic member 161 passes the low rigidity region 4A" includes a case in which the central part 164 of each leg portion elastic member 161 passes the thickness-wise outer surface Q side of the absorbent core 40, for example, the low rigidity region 4A passes a part corresponding to the low rigidity region A within the outer layer body 20 as in this embodiment. The central part 164 of each leg portion elastic member 161 refers to whole area of the leg portion elastic member 161 only excepting its opposite end portions 162, 163. It suffices that at least a part of the central part 164 passes a widthwise inside area of the side edge 141 of the absorbent core 40 in the crotch region C.

From the view point of surely enhancing the leak-preventive property, at least the area in the vicinity of the central portion of each leg portion elastic member 161 which divides the longitudinal direction of the leg portion elastic member 161 into two equal parts is located in the low rigidity region 4A. The length (length measured along the longitudinal direction of the diaper) L10 of the leg portion elastic member 161 passing the inside of the low rigidity region 4A is preferably from 10 to 50% and particularly preferably from 20 to 40% with respect to the entire length L11 of the absorbent core 40, and preferably from 5 to 40% and particularly preferably from 15 to 30% with respect to the longitudinal length L12 of the diaper 1D. The various values are based on the dimensions measured in a state that the joined side parts of the diaper are all peeled off each other and the diaper is developed and held in a tensioned state (the elastic members of the various parts are stretched, see FIG. 17).

In the disposable diaper 1D according to this embodiment, since the leg portion elastic member 161 is disposed in the manner as described above, a gap is hardly formed between the second absorbent core disposed portion (region where the second absorbent core 143 is disposed) 111 and the wearer's skin even at an area in the vicinity of the boundary between the stomach side region A and the crotch region C and at an area in the vicinity of the boundary between the back side region B and the crotch region C. Accordingly, no leak of excretions from the nearby areas of the two boundaries occurs. Moreover, since the leg portion elastic member 161 is disposed in the manner as described above, the diaper 1D is, as shown in FIG. 19, bent serving the part of arrangement of the leg portion elastic member 161 as a bending line and the area in the vicinity of the bent portion nicely fits to the inguinal part. Accordingly, even if the excretions migrate in the direction of the second absorbent core disposed portion 111 from the top of the central absorbent core 142, they are prohibited from migration by the nearby area of the bent portion. That is, this disposable diaper is more excellent in leak-preventive property.

The longitudinal length L13 of the second absorbent core 43 is preferably from ⅕ to ⅔ the longitudinal length L12 of the diaper. If the length of the second absorbent core 143 is in this range, the diaper is easily bent such that a sufficient length of the second absorbent core 143 is brought into contact with the wearer's leg area when the diaper is applied to the wearer. Accordingly, a gap is restrained from being formed between the leg area and the diaper and thus, the leak-preventive property is further enhanced. Although it is most preferable that the first and second elastic members 161a, 161b constituting the leg portion elastic members 161 are continuous in the crotch region C as in this embodiment, the two elastic members 161a, 161b may be slightly spaced apart from each other inasmuch as that the second absorbent core 143 is bent towards the backsheet 3 side and no gap is formed between the second absorbent core disposed portion and the wearer's skin. In this case, it is accepted that the end portions of the first and second elastic members 161a, 161b are located in the low rigidity region 4A and spaced apart from each other. It is also accepted that the first elastic members 161a on the left and right sides and the second elastic members 161b on the left and right sides may be continuous with each other through a communication part traversing the central absorbent core 142. It should be noted, however, that in the case where the elastic members 161a, 161b are spaced apart from each other, the spaced apart distance between them should be as small as possible taking into consideration the rigidity of the absorbent core because there is a possibility that the curved shape is adversely affected by the wearer's wearing state.

In the present invention, since the low rigidity regions 4A are disposed at opposite left and right sides of the absorbent core 4 and the central portion of each leg portion elastic member 161 passes the low rigidity region 4A, the absorbent core 40 can easily be bent, and the fitness to the wearer's leg area of the second absorbent core 143 can is enhanced. Thus, the leak-preventive property is readily exhibited. The method for forming the low rigidity region 4A is not particularly limited inasmuch as the rigidity of a part of the absorbent core can be made lower than the rigidity of the rest part. For example, there can be listed a method for cutting a part of the absorbent core 40 into a given shape, a method for making a part of the absorbent core 40 have a lower basis weight than the rest part, a method for making a part of the absorbent core 40 thinner than the rest part, a method for forming a part of the absorbent core 40 from a more flexible material than the rest part, a method of any combination thereof, and the like. As a method for forming the low rigidity regions 4A, 4A, a method according to this embodiment as later described or a method for cutting a part of the absorbent core 40 is preferable.

The low rigidity regions 4A, 4A of the diaper 1D according to this embodiment are formed by making the basis weight (weight per unit area) of the absorbent core in the region lower than that of the absorbent core in the adjacent part. The ratio (low rigidity region/inner side adjacent part) between the basis weight of the low rigidity region 4A, and the basis weight of the absorbent core in a part adjacent to an inner side thereof, and the ratio (low rigidity region/outer side adjacent part) between the basis weight of the low rigidity region 4A and the basis weight of the absorbent core in a part adjacent to an outer side thereof are preferably from 0 to 0.5. The difference is basis weight between the low rigidity region 4A and the inner side adjacent part, and between the low rigidity region 4A and the outer side adjacent part is preferably at least 100 g/m² or more and particularly preferably 200 g/m² or more.

In the diaper 1D according to this embodiment, the second absorbent core disposed portion elastic member 17 is disposed at the diaper outer surface Q side of the second absorbent core 143 and more specifically, at the diaper outer surface Q side of a part located at an outside area of the outer edge 44 of the low rigidity region 4A in the second absorbent core along the longitudinal direction of the second absorbent core 143. Moreover, the second absorbent core disposed side elastic members 18 are disposed at the opposite side edge portions of the absorbent core 40 along the opposite side edges 141, 141 of the absorbent core 40. The two elastic members 17, 18 in this embodiment are disposed from the stomach side region A over to the back side region B.

By providing the second absorbent core disposed portion elastic members 17 and/or the second absorbent core disposed side elastic members 18, fitness with respect to the leg area can be further enhanced, and thus, lead can be prevented more surely. However, in the case where the second absorbent core disposed portion elastic members 17 and/or the second absorbent core disposed side elastic members 18 are provided, if the elongation stress of those elastic members is large, there is a fear that the second absorbent cores are irregularly bent at an area other than the area where the leg portion elastic member is disposed and fitness to the leg area of the wearer is lowered. From the view point of preventing the above-mentioned inconvenience and surely enhancing the fitness to the leg area, the second absorbent core disposed portion elastic member 17 and/or the second absorbent core disposed side elastic member 18 are preferably lower in elongation stress than the leg portion elastic member 161.

In the case where the second absorbent core disposed portion elastic member 17 and the second absorbent core disposed side elastic member 18 are disposed at opposite sides of the diaper, or in the case where two or more of the elastic members 18 are disposed at opposite sides of the diaper, the total elongation stress of the elastic members 17, 18 disposed at one side of the diaper is preferably lower than the elongation stress of the leg portion elastic member 161 disposed at the same side. The elongation stress of the second absorbent core disposed portion elastic member 17, the second absorbent core disposed side elastic member 18 and the leg portion elastic member 161 can be measured as follows. Test pieces are cut out each having a longitudinal length of 100 mm in a shrunk state with respect to the second absorbent core disposed portion 111 and the low rigidity region A in the crotch region C of the diaper 1D and they are subjected to a tensile test using a tensile test machine (manufactured by Orientic Corp., 50 mm in chuck distance and 300 mm/min in test speed) and the stress at 25% stretching is measured. The results are converted in terms of the test piece width to obtain the respective elongation stresses.

Figure 20:
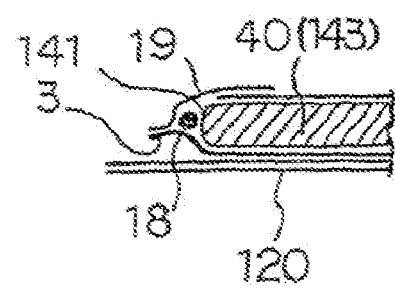
FIG. 20 is a sectional view of an important portion showing a disposable diaper according to another embodiment of the third invention.

The opposite side edges 141 of the absorbent core 40 in the diaper 1D according to this embodiment are covered with a water-repellent side sheet 19. Each side sheet is formed in the shape of belt. One side edge portion of each side sheet is joined to the topsheet 2 at the skin contact surface P side of the absorbent core 40, and the other side edge portion is joined to the backsheet 3 at the non-contact surface (same surface as the outer surface Q) side. Liquid ooze from the second absorbent core 143 can be prevented by covering with the side sheet 19. The other side edge portion of the side sheet 19, as shown in FIG. 20, may be joined to an extended part of the backsheet 3 which is extended from a side edge 141 of the absorbent core 40.

This disposable diaper 1D includes one pair of three-dimensional gathers 112, 112 which are formed from the stomach side region A over to the back side region B. Each three-dimensional gather 112 has a free end 113 at a widthwise inner side of the absorbent main body 10 and a fixed end (basal end) at an outer side. An elastic member 116 for forming the three-dimensional gather is fixedly arranged, in its stretched state, at the free end 113 of each three-dimensional gather 111 along the free end 113. Each three-dimensional gather 112 is provided by fixing the water-repellent gather forming sheet 115 having the elastic member 116 to the topsheet 2. The gather forming sheet 115 and the side sheet 19 are spaced apart from each other. Between those sheets 115 and 19, a side absorbent region 117 having a non-water-repellent surface is formed. Since the disposable diaper according to this embodiment has the above-mentioned construction, even if urine, etc. leak out beyond the arrangement part of the leg portion elastic member 161, they can be absorbed through the side absorbent region 117. Thus, the occurrence of leak can more surely be prevented.

In the disposable diaper 1D according to this embodiment, the first and second elastic members 161a, 161b forming one of the pair of left and right leg portion elastic members 161 and the first and second elastic members 161a, 161b forming the other are divided. Those elastic members are not present at least at the widthwise central part of the crotch region C. That is, the first and second elastic members 161a, 161b include a portion extending towards the central portion in a widthwise direction of the diaper from the portion for forming the leg portion elastic member 161. An end portion of the extended portion is located slightly inside of the side edge portion of the central absorbent core 142.

A plurality of body peripheral portion elastic members 118 are arranged at prescribed intervals on a body peripheral portion DS of the stomach side region A and back side region B. The body peripheral portion DS refers to a portion which is located bellow the position where the waist portion elastic member 151 is disposed but above the leg opening portions 16, 16 in a state that the waist opening portion 15 faces upward, as shown in FIG. 16. The body peripheral elastic members 118 are fixedly arranged at least at an outside area of the opposite side edges 141, 141 of the absorbent core such that elastic stretchability can be exhibited. At least at a widthwise central portion M of the portion where the absorbent core 40 exists, the body peripheral elastic members 118 are not arranged or no elastic stretchability is exhibited. The expression "no elastic stretchability is exhibited" refers to a state in which although the elastic member is arranged, elastic stretchability is lost at that portion by thermal treatment such as heat sealing or the like, or the stretched state is released so as not to exhibit elastic stretchability.

In the diaper 1D according to this embodiment, the elastic members 151, 161 and 181 are all fixed through an adhesive agent between the two sheet materials 21, 22 constituting the outer layer body 20, i.e., between the inner layer sheet 121 and the outer layer sheet 122 forming the outer surface.

The material for forming the component members of the disposable diaper 1D according to this embodiment will now be described. As the material for forming the topsheet 2, the backsheet 3, the absorbent core 40, the inner layer sheet 121, the outer layer sheet 122 and the like, those which has heretofore been used for disposable diapers or the like can be used without any particular limitation.

As the elastic members of the various portions, various kinds of elastic members which have heretofore been used for shorts type disposable diapers or the like can be used. As examples of the raw material for forming the elastic member, there can be listed, for example, synthetic rubber such as styrene-butadiene, butadiene, isoprene, neoprene and the like, natural rubber, EVA, expansible polyolefin, spandex, foam urethane, and the like. As examples of a form of the elastic member of the various portions, there can be used various kinds of forms. The form of the elastic members 151, 161 (161*a*, 161*b*) is preferably a belt-like one having a predetermined width (flat rubber, and the like). The form of the elastic member 118 is preferably a thread-like one (thread rubber and the like), while the form of the elastic members 17, 18, 116, a thread-like one (thread rubber or the like), a thread-like one having a predetermined width (flat rubber or the like) and a film-like one (urethane film or the like) are preferable.

As the material of the side sheet 19 and the three-dimensional gather forming sheet 115, various kinds of water-repellent sheet materials which have heretofore been used for shorts-type disposable diapers or the like can be used. For example, span bond nonwoven fabric, and span bond-melt blown-span bond nonwoven fabric are preferable.

The third invention is not limited to the above-mentioned embodiments and it can be changed and modified in accordance with necessity and without departing from the gist of the present invention. For example, the present invention can be applied not only to the shorts-type disposable diaper but also to a so-called flat-type disposable diaper in which a fastening tape is disposed at each opposite side edge portion of the back side region. The present invention can be applied to a disposable diaper in which the topsheet and the backsheet form the outer configuration of the diaper and which does not include an outer layer body. Instead of an arrangement in which a low rigidity region is provided, as in this embodiment, so that the diaper is easily bent at the position where the leg portion elastic member is disposed, it may be designed such that the second absorbent core is readily bent by reducing the rigidity of the whole absorbent core or by preliminarily providing a folding line. It suffices that the low rigidity region is spaced apart at least at a part thereof from the side edge of the absorbent core. For example, it is also accepted that the low rigidity region is curved in an arc-like shape such that the low rigidity region is spaced apart at its central portion from the side edge of the absorbent core but it reaches the side edge at its opposite end portions. The outer configuration of the absorbent core is not limited to a square shape but it may be formed in a trapezoidal shape and a hourglass shape. The configuration of the low rigidity region may be formed in a spindle shape, a square shape and the like. The leg portion elastic member is not limited to those which is composed of the first and second elastic members but it may be those which is composed of a single piece of elastic member.

In the disposable diaper of the third invention, the leg flap portion having a fluid absorptive/retentive performance can be closely fit to the wearer's skin. This diaper is excellent in fitness to the wearer's inguinal portion and capable of surely preventing leak around the leg area.

EXAMPLES

The present invention will now be illustrated in greater detail with reference to Examples. The following Examples are presented as being exemplary of the present invention and should not be considered as limiting.

Example 1

Figure 9:
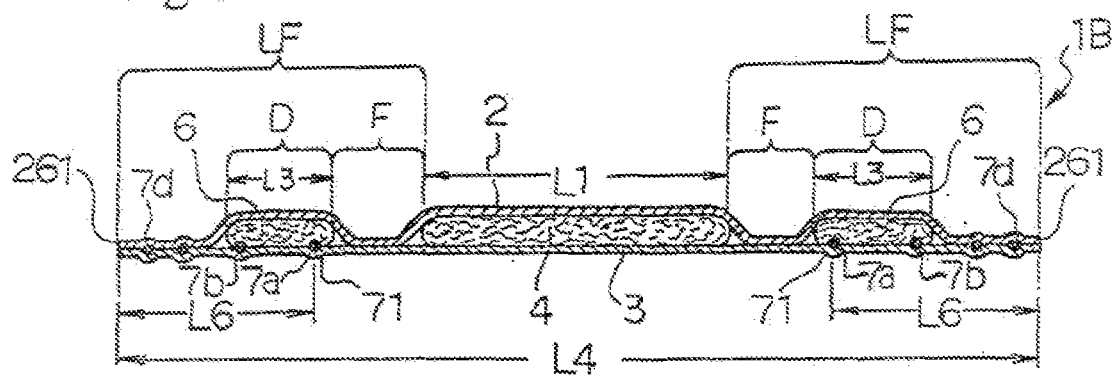
FIG. 9 is a schematic sectional view taken on line X-X of FIG. 8.
Figure 10:
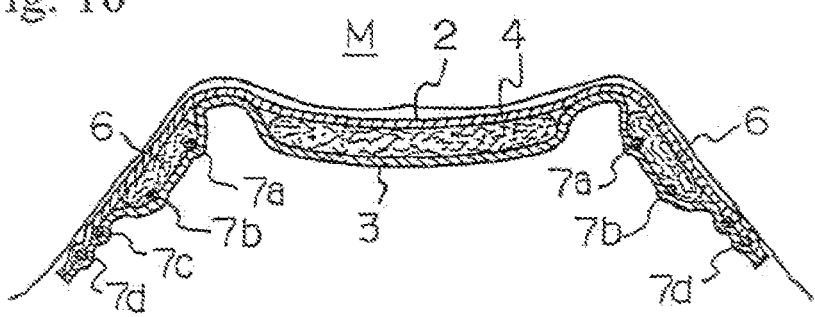
FIG. 10 is a schematic sectional view showing a worn state of the disposable diaper of FIG. 8.

A disposable diaper (example 1) of the form as shown in FIGS. 8 and 9 which have the dimensions and ratios as shown in Table 1.

Comparative Examples 1 to 3

A disposable diaper (comparative example 1) was prepared in the same manner as in the embodiment 1 only except that L7 in the example 1 was changed to from 57 to 100. A disposable diaper (comparative example 2) was prepared in the same manner as in the example 1 only except that L6 in the example 1 was changed to from 65 to 40. A disposable diaper (comparative example 3) was prepared in the same manner as in the example 1 only except that L7 in the example 1 was changed to from 57 to 100 and that L6 was changed from 65 to 40.

EVALUATION

With respect to the disposable diapers of examples and comparative examples, use test was conducted by 10 adult monitors for each. Based on the under-listed evaluation standard, the respective diapers were evaluated as to (a) whether or not a trunks-like shape is formed, (b) easiness to put on each diaper, (c) leak-preventive property, and (d) fitness. The results of evaluation are additionally shown in Table 1.

whether or not a Trunks-Like Shape is Formed:
    A: a trunks-like shape is formed
    B: not clear (a trunks-like shape can be formed, if tried very hard at the time of putting on the diaper)

C: definitely not a trunks-like shape easiness to Put on Each Diaper
- A: easy (8 monitors or more answered as easy)
- B: not clear (5 to 7 monitors answered as easy)
- C: not easy (4 monitors or less answered as easy)

leak-Preventive Property: Each diaper was applied to the human body model and have him/her laid on his/her side, and a physiological solution of sodium chloride of 150 g/times was caused to be excreted from the crotch region. Evaluation was made by checking the number of times until the solution leaks through the crotch region.
- S: 4 times or more
- A: 3 times
- B: 2 times
- C: Once fitness: Obtained answers as for whether or not the sense of fitness to the leg area is satisfactory and evaluation was made counting the number of monitors who answered as satisfactory.
- S: 9 or more monitors
- A: 7 to 8 monitors
- B: 5 to 6 monitors
- C: 4 or less monitors

TABLE 1

|  | Example | Comparative Examples | | |
|---|---|---|---|---|
|  | 1 | 1 | 2 | 3 |
| Smallest width L4 of crotch region | 420 | 430 | 430 | 430 |
| Largest width L5 of diaper | 640 | 640 | 640 | 640 |
| Shortest distance L6 between innermost side edge of leg portion elastic member and outer side edge of flap portion | 65 | 65 | 40 | 40 |
| Distance L7 between outermost side point and innermost side point of outer side edge of leg flap portion. | 57 | 100 | 57 | 100 |
| Longitudinal length L8 of crotch region | 420 | 420 | 420 | 420 |
| Region where outermost side point of outer side edge of leg flap portion exists | back side | back side | back side | back side |
| Presence of second absorbent core | yes | yes | yes | yes |
| Ratio   Ratio (L4/L5) | 0.66 | 0.67 | 0.67 | 0.67 |
| Ratio (L6/L4) | 0.13 | 0.15 | 0.09 | 0.09 |
| Ratio (L7/L8) | 0.14 | 0.24 | 0.13 | 0.23 |
| Evaluation   Whether or not a trunks-like shape is formed | A | B | C | C |
| Easiness to pat on diaper | A | C | B | C |
| Leak prevention (particularly at lying on one's side) | S | B | B | B |
| Fitness (particularly around legs) | S | B | C | C |

From the results shown in Table 1, it is known that the diapers of the examples take the shape of trunks during wearing the diaper, are excellent in leak-preventive property and designability, and are very easy to put on or apply. In contrast, the diapers of the comparative example do not take the shape of trunks because the ratios of some of them are not in the range of present invention or they are difficult to put on or apply even though they take the shape of trunks.

The invention being thus described, it will be obvious that the same may be varied in many ways. Such variations are not be regarded as a departure from the spirit and scope of the invention, and all such modification as would be obvious to one skilled in the art are intended to be included within the scope of the following claims.

This application claims the priority of Japanese Patent Application Nos. 2000-402839 filed Dec. 28, 2000, 2001-11155 filed Jan. 19, 2001, 2001-66189 filed Mar. 9, 2001 and 2001-178184 filed Jun. 13, 2001, which are incorporated herein by reference.

What is claimed is:

1. A disposable diaper comprising a fluid-permeable topsheet, a fluid-impermeable backsheet and a fluid-retentive absorbent core interposed between said topsheet and said backsheet, said disposable diaper having a stomach side, a back side and a crotch region positioned between said stomach side and said back side, leg portion elastic members being disposed in their stretched states at a pair of leg portions disposed around the wearer's leg areas, wherein lengthwise opposite end portions of said leg portion elastic members are located at widthwise outside areas of side edges of said absorbent core, respectively and central portions of said leg portion elastic members are curved in such a manner as to pass a widthwise inner direction of the side edges of said absorbent core at a crotch region of the diaper, said absorbent core at said crotch region of said diaper being divided into a pair of lateral absorbent cores located at widthwise outside areas of said leg portion elastic members, respectively, and a central absorbent core located between said pair of lateral absorbent cores by said pair of leg portion elastic members, said lateral absorbent cores are when in wear, being bent towards said backsheet and elastic members disposed below said lateral absorbent cores along the longitudinal direction of said diaper, wherein the elastic members are disposed at the diaper outer surface side or said lateral absorbent cores along a longitudinal direction of said lateral absorbent cores, and said elastic members are lower in elongation stress than said leg portion elastic members.

2. A disposable diaper comprising a fluid-permeable topsheet, a fluid-impermeable backsheet and a fluid-retentive absorbent core interposed between said topsheet and said backsheet, said disposable diaper having a stomach side, a back side and a crotch region positioned between said stomach side and said back side, leg portion elastic members being disposed in their stretched states at a pair of leg portions disposed wound the wearer's leg areas, wherein lengthwise opposite end portions of said leg portion elastic members are located at widthwise outside areas of side edges of said absorbent core, respectively and central portions of said leg portion elastic members are curved in such a manner as to pass a widthwise inner direction of the side edges of said absorbent core at a crotch region of the diaper, said absorbent core at said crotch region of said diaper being divided into a pair of lateral absorbent cores located at widthwise outside areas of said leg portion elastic members, respectively, and a central absorbent core located between said pair of lateral absorbent cores by said pair of leg portion elastic members, said lateral absorbent cores are when in wear, being bent towards said backsheet and elastic members disposed below said lateral absorbent cores along the longitudinal direction of said diaper, wherein leg flap side elastic members are disposed at the opposite side edge portions of said absorbent core at the crotch region of said diaper along the opposite side edges of said absorbent core, and said leg flap side elastic members are lower in elongation stress than said leg portion elastic members.

3. A disposable diaper comprising a fluid-permeable topsheet, a fluid-impermeable backsheet and a fluid-retentive absorbent core interposed between said topsheet and said backsheet, said disposable diaper having a stomach side, a back side and a crotch region positioned between said stomach side and said back side, leg portion elastic members being disposed in their stretched states at a pair of leg portions disposed around the wearer's leg areas, wherein lengthwise opposite end portions of said leg portion elastic members are located at widthwise outside areas of side edges of said absorbent core, respectively and central portions of said leg portion elastic members are curved in such a manner as to pass a widthwise inner direction of the side edges of said absorbent core at a crotch region of the diaper, said absorbent core at said crotch region of said diaper being divided into a pair of lateral absorbent cores located at widthwise outside areas of said leg portion elastic members, respectively, and a central absorbent core located between said pair of lateral absorbent cores by said pair of leg portion elastic members, said lateral absorbent cores are when in wear, being bent towards said backsheet and elastic members disposed below said lateral absorbent cores along the longitudinal direction of said diaper, wherein the opposite side edges of said absorbent core are covered with water-repellent side sheets, respectively, a pair of three-dimensional gathers are formed from a stomach side region to a back side region, each of said three-dimensional gathers being fixedly provided with a water-repellant gather forming sheet having an elastic member, said gather forming sheet and said side sheet being located away from each other, and a side absorption area having a non-water-repellent surface is formed between said gather forming sheet and said side sheet.

4. The disposable diaper according to claim 1, wherein a longitudinal length of said lateral absorbent cores is ⅕ to ⅔ of a longitudinal direction of said diaper.

5. The disposable diaper according to claim 2, wherein a longitudinal length of said lateral absorbent cores is ⅕ to ⅔ of a longitudinal direction of said diaper.

6. The disposable diaper according to claim 3, wherein a longitudinal length of said lateral absorbent cores is ⅕ to ⅔ of a longitudinal direction of said diaper.

7. The disposable diaper according to claim 1, wherein said absorbent core at the crotch region of said diaper includes a pair of lower rigidity regions, lower than the remaining regions, said pair of lower rigidity regions being located away from the opposite side edges of said absorbent core, and said leg portion elastic members are disposed such that their central portions pass said lower rigidity regions, respectively.

8. The disposable diaper according to claim 2, wherein said absorbent core at the crotch region of said diaper includes a pair of lower rigidity regions, lower than the remaining regions, said pair of lower rigidity regions being located away from the opposite side edges of said absorbent core, and said leg portion elastic members are disposed such that their central portions pass said lower rigidity regions, respectively.

9. The disposable diaper according to claim 3, wherein said absorbent core at the crotch region of said diaper includes a pair of lower rigidity regions, lower than the remaining regions, said pair of lower rigidity regions being located away from the opposite side edges of said absorbent core, and said leg portion elastic members are disposed such that their central portions pass said lower rigidity regions, respectively.

* * * * *